(12) United States Patent
Almansa-Rosales

(10) Patent No.: US 10,072,008 B2
(45) Date of Patent: Sep. 11, 2018

(54) SPIRO-ISOQUINOLINE-3,4'-PIPERIDINE COMPOUNDS HAVING ACTIVITY AGAINST PAIN

(71) Applicant: LABORATORIOS DEL DR. ESTEVE S.A., Barcelona (ES)

(72) Inventor: Carmen Almansa-Rosales, Barcelona (ES)

(73) Assignee: ESTEVE PHARMACEUTICALS S.A., Barcelona (ES)

( * ) Notice: Subject to any disclaimer, the term of this patent is extended or adjusted under 35 U.S.C. 154(b) by 0 days.

(21) Appl. No.: 15/569,939

(22) PCT Filed: Apr. 27, 2016

(86) PCT No.: PCT/EP2016/000676
§ 371 (c)(1),
(2) Date: Oct. 27, 2017

(87) PCT Pub. No.: WO2016/173710
PCT Pub. Date: Nov. 3, 2016

(65) Prior Publication Data
US 2018/0155343 A1 Jun. 7, 2018

(30) Foreign Application Priority Data
Apr. 28, 2015 (EP) .................................... 15382210

(51) Int. Cl.
| C07D 471/10 | (2006.01) |
| A61P 25/04 | (2006.01) |
| A61P 25/00 | (2006.01) |
| A61P 29/00 | (2006.01) |

(52) U.S. Cl.
CPC ............ C07D 471/10 (2013.01); A61P 25/00 (2018.01); A61P 25/04 (2018.01); A61P 29/00 (2018.01)

(58) Field of Classification Search
CPC .................................................... C07D 471/10
See application file for complete search history.

(56) References Cited

U.S. PATENT DOCUMENTS 5,206,240 A * 4/1993 Baldwin .............. C07D 221/20
514/231.5

FOREIGN PATENT DOCUMENTS

| EP | 1634873 | 3/2006 |
| EP | 1847542 | 10/2007 |
| WO | WO 01/12830 A1 | 2/2001 |
| WO | WO 2007/098961 | 9/2007 |
| WO | WO 2009/071657 | 6/2009 |

OTHER PUBLICATIONS

International Search Report for PCT/EP2016/000676 dated May 23, 2016.
Bowen W.D., Pharmaceutica Acta Helvetiae, (2002) 74: 211-218.
G. Ronsisvalie et al., Pure Appl. Chem., 73, 1499-1509 (2001).
Hanner, M. et al., Proc. Natl. Acad. Sci., 1996, 93:8072-8077.
Kaiser et al., Neurotransmissions, 1991, 7 (1): 1-5.
Quirion, R. et al., Trends Pharmacol. Sci., 1992, 13:85-86.
Snyder, S.H., Largent, B.L., J. Neuropsychiatry, 1989, 1, 7.
Walker, J.M. et al., Pharmacological Reviews, 1990, 42, 355.

* cited by examiner

*Primary Examiner* — Laura L Stockton
(74) *Attorney, Agent, or Firm* — Hueschen and Sage

(57) ABSTRACT

The present invention relates to compounds having pharmacological activity towards the sigma (σ) receptor, and more particularly to spiro-isoquinoline-3,4'-piperidine compounds having this pharmacological activity, to processes of preparation of such compounds, to pharmaceutical compositions comprising them, and to their use in therapy, in particular for the treatment of pain.

19 Claims, No Drawings

SPIRO-ISOQUINOLINE-3,4'-PIPERIDINE COMPOUNDS HAVING ACTIVITY AGAINST PAIN

FIELD OF THE INVENTION

The present invention relates to new spiro-isoquinoline-3,4'-piperidine compounds having a great affinity for sigma receptors, especially sigma-1 ($\sigma_1$) receptors, as well as to the process for the preparation thereof, to compositions comprising them, and to their use as medicaments.

BACKGROUND OF THE INVENTION

The search for new therapeutic agents has been greatly aided in recent years by better understanding of the structure of proteins and other biomolecules associated with target diseases. One important class of these proteins are the sigma ($\sigma$) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF-10047, (+)cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. (+)SKF-10047 has nanomolar affinity for the sigma-1 ($\sigma_1$) site, and has micromolar affinity for the sigma-2 ($\sigma_2$) site. Haloperidol has similar affinities for both subtypes.

The $\sigma_1$ receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for (+)SKF-10047, (+)-pentazocine, haloperidol and rimcazole, among others, known ligands with analgesic, anxiolytic, antidepressive, antiamnesic, antipsychotic and neuroprotective activity. $\sigma_1$ receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M et al, Pharmacological Reviews, 1990, 42, 355] and [Bowen W. D. (2000) Pharmaceutica Acta Helvetiae 74: 211-218].

The $\sigma_2$ receptor is also expressed in numerous adult mammal tissues (e.g. nervous system, immune system, endocrine system, liver, kidney). $\sigma_2$ receptors can be components in a new apoptosis route that may play an important role in regulating cell proliferation or in cell development. This route seems to consist of $\sigma_2$ receptors joined to intracellular membranes, located in organelles storing calcium, such as the endoplasmic reticulum and mitochondria, which also have the ability to release calcium from these organelles. The calcium signals can be used in the signaling route for normal cells and/or in induction of apoptosis.

Agonists of $\sigma_2$ receptors induce changes in cell morphology, apoptosis in several types of cell lines and regulate the expression of p-glycoprotein mRNA, so that they are potentially useful as antineoplasic agents for treatment of cancer. In fact, $\sigma_2$ receptor agonists have been observed to induce apoptosis in mammary tumour cell lines resistant to common antineoplasic agents that damage DNA. In addition, agonists of $\sigma_2$ receptors enhance the cytotoxic effects of these antineoplasic agents at concentrations in which the agonist is not cytotoxic. Thus, agonists of $\sigma_2$ receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of $\sigma_2$ receptors can prevent the irreversible motor side effects caused by typical neuroleptic agents. In fact, it has been found that antagonists of $\sigma_2$ receptors can be useful as agents for improving the weakening effects of delayed dyskinesia appearing in patients due to chronic treatment of psychosis with typical antipsychotic drugs, such as haloperidol. $\sigma_2$ receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2009/071657 discloses some tricyclic triazolic compounds although structurally different to the ones of the current invention with activity towards sigma receptors.

Nevertheless, there is still a need to find compounds having pharmacological activity towards the sigma receptor, being both effective, selective, and/or having good "drugability" properties, i.e. good pharmaceutical properties related to administration, distribution, metabolism and excretion.

Surprisingly, it has been observed that the new spiro-isoquinoline-3,4'-piperidine compounds with general Formula (I) show an affinity for $\sigma_1$ receptor ranging from good to excellent. These compounds are therefore particularly suitable as pharmacologically active agents in medicaments for the prophylaxis and/or treatment of disorders or diseases related to Sigma receptors.

SUMMARY OF THE INVENTION

The present invention discloses novel compounds with great affinity to sigma receptors and having high solubility in a physiological media which might be used for the treatment of sigma related disorders or diseases.

As this invention is aimed at providing a compound or a chemically related series of compounds which act as ligands of the $\sigma_1$ receptor it is a very preferred embodiment if the compound has a binding expressed as $K_i$ which is preferably <1000 nM, more preferably <500 nM, even more preferably <100 nM.

The invention is directed in a main aspect to a compound of general Formula (I),

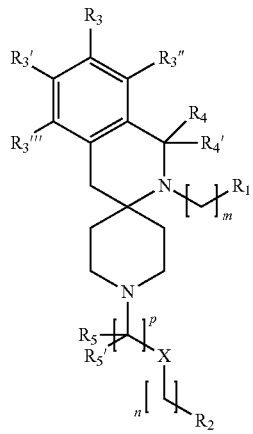

wherein $R_1$, $R_2$, $R_3$, $R_{3'}$, $R_{3''}$, $R_{3'''}$, $R_4$, $R_{4'}$, $R_5$, $R_{5'}$, X, m, n and p are as defined below in the detailed description.

A further object of the invention refers to the processes for preparation of compounds of general formula (I).

A still further object of the invention refers to the use of intermediate compounds for the preparation of a compound of general formula (I).

It is also an object of the invention a pharmaceutical composition comprising a compound of formula (I).

Finally, it is an object of the invention the use of compound as a medicament and more particularly for the treatment of pain and pain related conditions.

DETAILED DESCRIPTION OF THE INVENTION

The invention is directed to a family of structurally distinct spiro-isoquinoline-3,4'-piperidine derivatives which have a pharmacological activity towards the sigma (σ) receptor, thus solving the above problem.

In a particular aspect, the present invention is directed to compounds of general Formula (I):

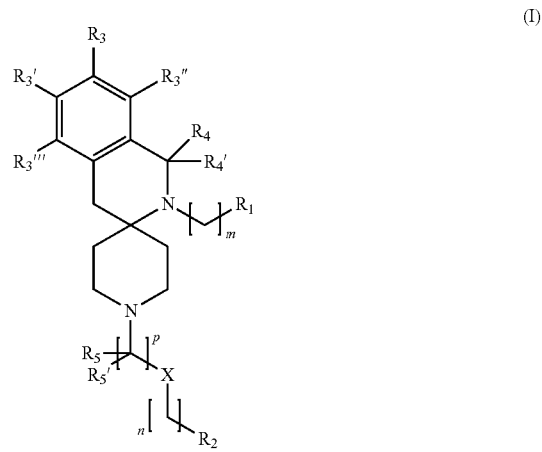

wherein
m is 0, 1, 2, 3, 4, 5 or 6;
n is 0, 1, 2, 3 or 4;
p is 1, 2, 3 or 4;
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, —C(O)R$_6$, —C(O)OR$_6$, —C(O)NR$_6$R$_{6'}$ and —S(O)$_2$R$_6$;
  wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, and substituted or unsubstituted heterocyclyl or substituted or unsubstituted alkyheterocylcyl;
$R_2$ is selected from substituted or unsubstituted cycloalkyl, substituted or unsubstituted aryl and substituted or unsubstituted heterocyclyl;
X is selected from a bond, —C(R$_x$R$_{x'}$)— and —C(R$_x$) (OR$_7$)—;
$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_{7'}$, —NR$_7$C(O)R$_7$, and —NR$_7$R$_{7''}$;
$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;
and wherein $R_{7'''}$ is selected from hydrogen, unsubstituted $C_{1-6}$ alkyl, unsubstituted $C_{2-6}$ alkenyl, unsubstituted $C_{2-6}$ alkynyl and —Boc;
$R_3$ is selected from hydrogen, halogen, —R$_9$, —OR$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —NR$_9$S(O)$_2$R$_9$R$_{9''}$ and —OC(O)R$_9$;
$R_{3'}$, $R_{3''}$ and $R_{3'''}$ are independently selected from hydrogen, halogen, —R$_9$, —NO$_2$, —NR$_9$R$_{9'''}$, —NR$_9$C(O)R$_{9'}$, —NC(O)OR$_9$, —NR$_9$S(O)$_2$R$_{9'}$, —S(O)$_2$NR$_9$R$_{9'}$, —NR$_9$C(O)NR$_9$,R$_{9''}$, —SR$_9$, —S(O)R$_9$, —S(O)$_2$R$_9$, —CN, haloalkyl, haloalkoxy, —C(O)OR$_9$, —C(O)NR$_9$R$_{9'}$, —NR$_9$S(O)$_2$NR$_9$,R$_{9''}$ and —OC(O)R$_9$;

wherein R$_9$, R$_{9'}$ and R$_{9''}$ are independently selected from hydrogen, unsubstituted C$_{1-6}$ alkyl, unsubstituted C$_{2-6}$ alkenyl, and unsubstituted C$_{2-6}$ alkynyl;

and wherein R$_{9'''}$ is selected from hydrogen, unsubstituted C$_{1-6}$ alkyl, unsubstituted C$_{2-6}$ alkenyl, unsubstituted C$_{2-6}$ alkynyl and —Boc;

R$_4$ is selected from hydrogen, —OR$_8$, substituted or unsubstituted C$_{1-6}$ alkyl, substituted or unsubstituted C$_{2-6}$ alkenyl, substituted or unsubstituted C$_{2-6}$ alkynyl, —C(O)OR$_8$, —C(O)NR$_8$R$_{8'}$, —NR$_8$C(O)R$_{8'}$, —NR$_8$R$_{8'''}$ and —NC(O)OR$_8$;

R$_{4'}$ is selected from hydrogen, or substituted or unsubstituted C$_{1-6}$ alkyl, substituted or unsubstituted C$_{2-6}$ alkenyl, and substituted or unsubstituted C$_{2-6}$ alkynyl;

wherein R$_8$, R$_{8'}$ and R$_{8''}$ are independently selected from hydrogen, unsubstituted C$_{1-6}$ alkyl, unsubstituted C$_{2-6}$ alkenyl, and unsubstituted C$_{2-6}$ alkynyl;

and wherein R$_{8'''}$ is selected from hydrogen, unsubstituted C$_{1-6}$ alkyl, unsubstituted C$_{2-6}$ alkenyl, unsubstituted C$_{2-6}$ alkynyl and —Boc;

alternatively, R$_4$ and R$_{4'}$ may form together with the carbon to which they are attached, a C═O group;

R$_5$ and R$_{5'}$ are independently selected from hydrogen, or substituted or unsubstituted C$_{1-6}$ alkyl, substituted or unsubstituted C$_{2-6}$ alkenyl, and substituted or unsubstituted C$_{2-6}$ alkynyl;

These compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a particular embodiment the following compound is excluded:

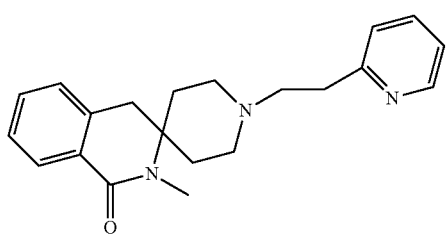 [SMILES: CN1C(=O)c2ccccc2CC12CCN(CCc1ccccn1)CC2]

In another particular embodiment the aryl in R$_2$ is not substituted with —NR$_{12}$S(O)$_2$R$_{12''}$.

In another particular embodiment if R$_4$ and R$_{4'}$ form together with the carbon to which they are attached, a C═O group, then —(CH$_2$)$_m$—R$_1$ has to be "H".

In a further embodiment the compound according to the invention of general Formula (I) is a compound of general Formula (I')

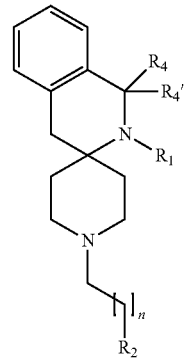

wherein R$_1$, R$_2$, R$_4$, R$_{4'}$ and n are as defined in the description.

In a further embodiment the compound according to the invention of general Formula (I) is a compound of general Formula (I$^{2'}$)

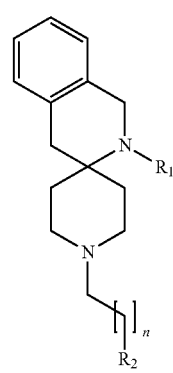

wherein R$_1$, R$_2$ and n are as defined in the description.

In a further embodiment the compound according to the invention of general Formula (I) is a compound of general Formula (I$^{3'}$)

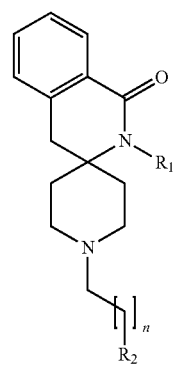

I$^{3'}$ wherein R$_1$, R$_2$ and n are as defined in the description.

In a further embodiment the compound according to the invention of general Formula (I) is a compound of general Formula (I$^{4'}$)

(I⁴')

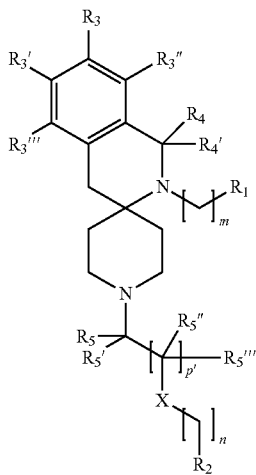

wherein R₁, R₂, R₃, R₃', R₃'', R₃''', R₄, R₄', R₅, R₅', m, n and X are as defined in the description. In addition, p', R₅'' and R₅''' are added. These are reflecting the statements below in the definitions of substituitions on alkyl etc. or aryl etc. that "when different radicals R₁ to R₁₃''' and R_x are present simultaneously in Formula I they may be identical or different". Thus this is reflecting that R₅'' and R₅''' are or could be different from R₅ and R₅' or not and—accordingly—p' being 0 or 1, 2 or 3 is naturally resulting from p being 1, 2, 3 or 4.

For clarity purposes, all groups and definitions described in the present description and referring to compounds of general Formula (I), also apply to compounds of general Formula (I'), (I²'), (I³') or (I⁴') (where applicable), since compounds of general Formula (I'), (I²'), (I³') or (I⁴') are included within the scope of the larger definition of general Formula (I).

For clarity purposes, the general Markush Formula (I)

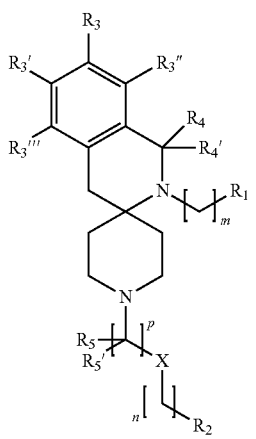

is equivalent to

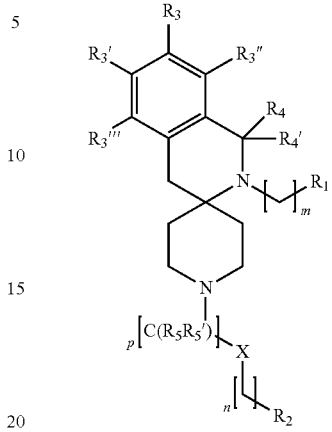

wherein only —C(R₅R₅')— are included into the brackets and p means the number of times that —C(R₅R₅')— is repeated. The same would apply to general Markush Formulae (I'), (I²'), (I³'), (I⁴') or (I⁵').

In addition, and for clarity purposes, it should further be understood that naturally if n is 0, R₂ is still present in general Markush Formulae (I), (I'), (I²'), (I³') or (I⁴').

In the context of this invention, alkyl is understood as meaning saturated, linear or branched hydrocarbons, which may be unsubstituted or substituted once or several times. It encompasses e.g. —CH₃ and —CH₂—CH₃. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also CHF₂, CF₃ or CH₂OH etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH═CH—CH₃. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—CH₃ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), —$NR_cR_{c'''}$, —$SR_c$, —$S(O)R_c$, —$S(O)_2R_c$, —$OR_c$, —$C(O)OR_c$, —CN, —$C(O)NR_cR_{c'}$, haloalkyl, haloalkoxy or —$OC_{1-4}$alkyl being unsubstituted or substituted by one or more of —$OR_c$ or halogen (F, Cl, I, Br), being $R_c$ represented by $R_{11}$, $R_{12}$, $R_{10}$, (being $R_{c'}$ represented by $R_{11'}$, $R_{12'}$, $R_{10'}$; being $R_{c''}$ represented by $R_{11''}$, $R_{12''}$, $R_{10''}$; being $R_{c'''}$ represented by $R_{11'''}$, $R_{12'''}$, $R_{10'''}$), being $R_{c''''}$ represented by $R_{11''''}$, $R_{12''''}$, $R_{10''''}$) wherein $R_1$ to $R_{13''''}$ and $R_x$ are as defined in the description, and wherein when different radicals $R_1$ to $R_{13''''}$ and $R_x$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which is substituted is substituted with one or more of halogen (F, Cl, Br, I), —$OR_c$, —CN, —$SR_c$, —$S(O)R_c$, and —$S(O)_2R_c$, haloalkyl, haloalkoxy or —$OC_{1-4}$alkyl being unsubstituted or substituted by one or more of —$OR_c$ or halogen (F, Cl, I, Br), being $R_c$ represented by $R_{11}$, $R_{12}$, $R_{10}$, (being $R_{c'}$ represented by $R_{11'}$, $R_{12'}$, $R_{10'}$; being $R_{c''}$ represented by $R_{11''}$, $R_{12''}$, $R_{10''}$; being $R_{c'''}$ represented by $R_{11'''}$, $R_{12'''}$, $R_{10'''}$, being $R_{c''''}$ represented by $R_{11''''}$, $R_{12''''}$, $R_{10''''}$), wherein $R_1$ to $R_{13''''}$ and $R_x$ are as defined in the description, and wherein when different radicals $R_1$ to $R_{13''''}$ and $R_x$ are present simultaneously in Formula I they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHCl_2$. Preferably haloalkyl is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl or indanyl, 9H-fluorenyl or anthracenyl radicals, which can be unsubstituted or once or several times substituted. Most preferably aryl is understood in the context of this invention as phenyl, naphthyl or anthracenyl, preferably is phenyl.

A heterocyclyl radical or group (also called heterocyclyl hereinafter) is understood as meaning 5 to 18 membered mono or polycyclic heterocyclic ring systems, with at least one saturated or unsaturated ring which contains one or more heteroatoms from the group consisting of nitrogen, oxygen and/or sulfur in the ring. A heterocyclic group can also be substituted once or several times.

Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered mono or polycyclic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic 5 to 18 membered mono or polycyclic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, especially is benzodioxane, morpholine, tetrahydropyran, piperidine, oxopyrrolidine and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3]pyridine, benzoxazole, oxopyrrolidine, pyrimidine, oxazepane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_{c'}$, —$C(O)NR_cR_{c'}$, —$NR_cS(O)_2R_{c'}$, =O, —$OCH_2CH_2OH$, —$NR_cC(O)NR_cR_{c'''}$, —$S(O)_2NR_cR_{c'}$, —$NR_cS(O)_2NR_cR_{c'''}$, haloalkyl, haloalkoxy, —$S(O)R_c$, —$S(O)R_c$, —$S(O)_2R_c$ or $C(CH_3)OR_c$; $NR_cR_{c'''}$, with $R_c$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{13}$, (being $R_{c'}$ one of $R_{11'}$, $R_{12'}$ or $R_{13'}$; being $R_{c''}$ one of $R_{11''}$, $R_{12''}$ or $R_{13''}$; being $R_{c'''}$ one of $R_{11'''}$, $R_{12'''}$ or $R_{13'''}$; being $R_{c''''}$ one of $R_{11''''}$, $R_{12''''}$ or $R_{13''''}$), wherein $R_1$ to $R_{13''''}$ and $R_x$ are as defined in the description, and wherein when different radicals $R_1$ to $R_{13''''}$ and $R_x$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, —$S(O)_2NR_cR_{c'}$, —$NR_cC(O)NR_cR_{c''}$, haloalkyl, haloalkoxy, —$SR_c$, —$S(O)R_c$ or $S(O)_2R_c$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_{11}$, $R_{12}$ or $R_{13}$, (being $R_{c'}$ one of $R_{11'}$, $R_{12'}$ or $R_{13'}$; being $R_{c''}$ one of $R_{11''}$, $R_{12''}$ or $R_{13''}$; being $R_{c'''}$ one of $R_{11'''}$, $R_{12'''}$ or $R_{13'''}$; being $R_{c''''}$ one of $R_{11''''}$, $R_{12''''}$ or $R_{13''''}$), wherein $R_1$ to $R_{13'''}$ and $R_x$ are as defined in the description, and wherein when different radicals $R_1$ to $R_{13''''}$ and $R_x$ are present simultaneously in Formula I they may be identical or different.

In connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

(leading to a spiro structure) or =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a further embodiment the compound according to the invention of general Formula (I) is a compound wherein
m is 0, 1, 2, 3, 4, 5 or 6;
n is 0, 1, 2, 3 or 4;
p is 1, 2, 3 or 4;
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, —C(O)$R_6$, —C(O)O$R_6$, —C(O)N$R_6R_{6'}$ and —S(O)$_2R_6$;
wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, and substituted or unsubstituted heterocyclyl or substituted or unsubstituted alkyheterocylcyl;

wherein said cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, — and —$NR_{11}S(O)_2NR_{11'}R_{11''}$;

wherein said cycloalkyl or non-aromatic heterocyclyl in $R_1$ or $R_6$, also in alkylcycloalkyl and alkylheterocyclyl, if substituted, may also be substituted with

or =O;

wherein the alkyl, alkenyl or alkynyl in $R_1$ or $R_6$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl; and wherein $R_{11'''}$ is selected from hydrogen, unsubstituted $C_{1-6}$ alkyl, unsubstituted $C_{2-6}$ alkenyl, unsubstituted $C_{2-6}$ alkynyl and —Boc;

$R_2$ is selected from substituted or unsubstituted cycloalkyl, substituted or unsubstituted aryl and substituted or unsubstituted heterocyclyl;

wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$S(O)_2NR_{12}R_{12'}$, —$NR_{12}C(O)NR_{12'}R_{12''}$, —$SR_{12}$, —$S(O)R_{12}$, $S(O)_2R_{12}$, —CN, haloalkyl, haloalkoxy, —$C(O)OR_{12}$, —$C(O)NR_{12}R_{12'}$, and —$NR_{12}S(O)_2NR_{12'}R_{12''}$;

wherein said cycloalkyl or non-aromatic heterocyclyl in $R_2$, if substituted, may also be substituted with

or =O;

wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;

wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and —Boc;

X is selected from a bond, —$C(R_xR_{x'})$— and —$C(R_x)(OR_7)$—;

$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —$C(O)OR_7$, —$C(O)NR_7R_{7'}$, —$NR_7C(O)R_{7'}$, and —$NR_7R_{7''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and —Boc;

$R_3$ is selected from hydrogen, halogen, —$R_9$, —$OR_9$, —$NO_2$, —$NR_9R_{9'''}$, —$NR_9C(O)R_{9'}$, —$NC(O)OR_9$, —$NR_9S(O)_2R_{9'}$, —$S(O)_2NR_9R_{9'}$, —$NR_9C(O)NR_9R_{9'''}$, —$SR_9$, —$S(O)R_9$, —$S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

$R_{3'}$, $R_{3''}$ and $R_{3'''}$ are independently selected from hydrogen, halogen, —$R_9$, —$NO_2$, —$NR_9R_{9'''}$, —$NR_9C(O)R_{9'}$, —$NC(O)OR_9$, —$NR_9S(O)_2R_{9'}$, —$S(O)_2NR_9R_{9'}$, —$NR_9C(O)NR_9R_{9'''}$, —$SR_9$, —$S(O)R_9$, —$S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and —Boc;

$R_4$ is selected from hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$, —$NR_8C(O)R_{8'}$, —$NR_8R_{8'''}$ and —$NC(O)OR_8$;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and —Boc;

alternatively, $R_4$ and $R_{4'}$ may form together with the carbon to which they are attached, a C=O group;

$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

the alkyl, alkenyl or alkynyl, other than those defined in $R_1$, $R_2$ or $R_6$, if substituted, is substituted with one or more substituent/s selected from —$OR_{10}$, halogen, —CN, haloalkyl, haloalkoxy, —$SR_{10}$, —$S(O)R_{10}$, and —$S(O)_2R_{10}$;

wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

the aryl, heterocyclyl or cycloalkyl, also in alkylaryl, alkylcycloalkyl and alkylheterocyclyl, other than those defined in $R_1$, $R_2$ or $R_6$, if substituted, is substituted with one or more substituent/s selected from halogen, —$R_{13}$, —$OR_{13}$, —$NO_2$, —$NR_{13}R_{13'''}$, $NR_{13}C(O)R_{13'}$, —$NR_{13}S(O)_2R_{13'}$, —$S(O)_2NR_{13}R_{13'}$, —$NR_{13}C(O)NR_{13'}R_{13''}$, —$SR_{13}$, —$S(O)R_{13}$, $S(O)_2R_{13}$, —CN, haloalkyl, haloalkoxy, —$C(O)OR_{13}$, —$C(O)NR_{13}R_{13'}$, —$OCH_2CH_2OH$, —$NR_{13}S(O)_2NR_{13'}R_{13''}$ and $C(CH_3)_2OR_{13}$;

wherein cycloalkyl or non-aromatic heterocyclyl, other than those defined in $R_1$, $R_2$ or $R_6$, also in alkylcycloalkyl and alkylheterocyclyl, if substituted, may also be substituted with

or =O;
- wherein $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;
- and wherein $R_{13'''}$ is selected from hydrogen, unsubstituted $C_{1-6}$ alkyl, unsubstituted $C_{2-6}$ alkenyl, unsubstituted $C_{2-6}$ alkynyl and —Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
m is 0, 1, 2, 3, 4, 5 or 6;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
n is 0, 1, 2, 3 or 4;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein
p is 1, 2, 3 or 4;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is selected from a bond, —C($R_xR_x$)— and —C($R_x$)(O$R_7$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
X is selected from a bond and —C($R_xR_x$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, —C(O)$R_6$, —C(O)O$R_6$, —C(O)N$R_6R_{6'}$ and —S(O)$_2R_6$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and —C(O)$R_6$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_1$ is selected from hydrogen, substituted or unsubstituted $C_{1-6}$ alkyl and —C(O)$R_6$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from substituted or unsubstituted aryl; preferably substituted or unsubstituted phenyl, more preferably unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein $R_2$ is substituted or unsubstituted heterocyclyl, preferably substituted or unsubstituted morpholine, more preferably unsubstituted morpholine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —$OR_9$, —$NO_2$, —$NR_9R_{9'''}$, —$NR_9C(O)R_{9'}$, —$NC(O)OR_9$, —$NR_9S(O)_2R_{9'}$, —$S(O)_2NR_9R_{9'}$, —$NR_9C(O)NR_9R_{9''}$, —$SR_9$, —$S(O)R_9$, —$S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

$R_{3'}$, $R_{3''}$ and $R_{3'''}$ are independently selected from hydrogen, halogen, —$R_9$, —$NO_2$, —$NR_9R_{9'''}$, —$NR_9C(O)R_{9'}$, —$NC(O)OR_9$, —$NR_9S(O)_2R_{9'}$, —$S(O)_2NR_9R_{9'}$, —$NR_9C(O)NR_9R_{9''}$, —$SR_9$, —$S(O)R_9$, —$S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —$OR_9$, —$NO_2$, —$NR_9R_{9'''}$, —$NR_9C(O)R_{9'}$, —$NC(O)OR_9$, —$NR_9S(O)_2R_{9'}$, —$S(O)_2NR_9R_{9'}$, —$NR_9C(O)NR_9R_{9''}$, —$SR_9$, —$S(O)R_9$, —$S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_{3'}$, $R_{3''}$ and $R_{3'''}$ are independently selected from hydrogen, halogen, —$R_9$, —$NO_2$, —$NR_9R_{9'''}$, —$NR_9C(O)R_{9'}$, —$NC(O)OR_9$, —$NR_9S(O)_2R_{9'}$, —$S(O)_2NR_9R_{9'}$, —$NR_9C(O)NR_9R_{9''}$, —$SR_9$, —$S(O)R_9$, —$S(O)_2R_9$, —CN, haloalkyl, haloalkoxy, —$C(O)OR_9$, —$C(O)NR_9R_{9'}$, —$NR_9S(O)_2NR_9R_{9''}$ and —$OC(O)R_9$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —$OR_9$, and —$NR_9R_{9'''}$;

$R_{3'}$, $R_{3''}$ and $R_{3'''}$ are independently selected from hydrogen, halogen, —$R_9$, and —$NR_9R_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —$OR_9$, and —$NR_9R_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_{3'}$, $R_{3''}$ and $R_{3'''}$ are independently selected from hydrogen, halogen, —$R_9$, and —$NR_9R_{9'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ is selected from hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$, —$NR_8C(O)R_{8'}$, —$NR_8R_{8'''}$ and —$NC(O)OR_8$;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ is selected from hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —$C(O)OR_8$, —$C(O)NR_8R_{8'}$, —$NR_8C(O)R_{8'}$, —$NR_8R_{8'''}$ and —$NC(O)OR_8$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ may form together with the carbon to which they are attached, a C=O group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, and substituted or unsubstituted heterocyclyl or substituted or unsubstituted alkyheterocylcyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{7'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{8'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{9'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;
- and wherein $R_{13'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- $R_{13}$, $R_{13'}$ and $R_{13''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- $R_{13'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_7'$, —NR$_7$C(O)R$_7'$, and —NR$_7$R$_{7'''}$;
- $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_7'$, —NR$_7$C(O)R$_7'$, and NR$_7$R$_{7'''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- X is —C(R$_x$R$_{x'}$)—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- X is —CH$_2$—;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- m is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
- n is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein m is 0 or 1, n is 0 or 1 and p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, or —C(O)$R_6$;

and wherein $R_6$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_2$ is selected from substituted or unsubstituted aryl and substituted or unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein X is selected from a bond and —(CR$_x$R$_{x'}$)—; and wherein R$_x$ is selected from hydrogen, substituted or unsubstituted $C_{1-6}$ alkyl, substituted or unsubstituted $C_{2-6}$ alkenyl, and substituted or unsubstituted $C_{2-6}$ alkynyl;

R$_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_3$ is selected from hydrogen, halogen, —$R_9$, —O$R_9$, and —N$R_9R_{9'''}$; and $R_{3'}$, $R_{3''}$ and $R_{3'''}$ are independently selected from hydrogen, halogen, —$R_9$, and —N$R_9R_{9'''}$;

and wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

$R_{9'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_4$ is selected from hydrogen, —O$R_8$, substituted or unsubstituted $C_{1-6}$ alkyl;

$R_{4'}$ is selected from hydrogen, or substituted or unsubstituted $C_{1-6}$ alkyl;

and wherein $R_8$ is unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein $R_4$ and $R_{4'}$ form together with the carbon to which they are attached, a C=O group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0 or 1; and n is 0 or 1; and p is 1; and $R_1$ is selected from hydrogen, substituted or unsubstituted $C_{1-6}$ alkyl, preferably substituted or unsubstituted methyl, and —C(O)$R_6$;

and $R_2$ is selected from substituted or unsubstituted aryl, preferably substituted or unsubstituted phenyl, and substituted or unsubstituted heterocyclyl, preferably substituted or unsubstituted morpholine;

and

X is a bond;

and $R_3$, $R_{3'}$, $R_{3''}$ and $R_{3'''}$ are all hydrogen;

and $R_4$ and $R_{4'}$ are both hydrogen, or may form together with the carbon to which they are attached, a C=O group;

and $R_5$ and $R_{5'}$ are both hydrogen;

and $R_6$ is substituted or unsubstituted $C_{1-6}$ alkyl, preferably substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0 or 1; and/or n is 0 or 1; and/or p is 1; and/or $R_1$ is selected from hydrogen, substituted or unsubstituted $C_{1-6}$ alkyl, preferably substituted or unsubstituted methyl, and —C(O)$R_6$;

and/or $R_2$ is selected from substituted or unsubstituted aryl, preferably substituted or unsubstituted phenyl, more preferably unsubstituted phenyl, and substituted or unsubstituted heterocyclyl, preferably substituted or unsubstituted morpholine;

and/or

X is a bond;

and/or $R_3$, $R_{3'}$, $R_{3''}$ and $R_{3'''}$ are all hydrogen;

and/or $R_4$ and $R_{4'}$ are both hydrogen, or may form together with the carbon to which they are attached, a C=O group;

and/or $R_5$ and $R_{5'}$ are both hydrogen;

and/or $R_6$ is substituted or unsubstituted $C_{1-6}$ alkyl, preferably substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, p is 1, X is a bond, and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, p is 1, X is a bond, and $R_2$ is substituted or unsubstituted morpholine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 0, p is 1, X is a bond, and $R_2$ is substituted or unsubstituted phenyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond and $R_1$ is hydrogen, substituted or unsubstituted methyl or substituted or unsubstituted acetyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 0, m is 0, p is 1, X is a bond and $R_1$ is hydrogen or substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond, and $R_1$ is —C(O)$R_6$, wherein $R_6$ is substituted or unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 1, m is 0, p is 1, X is a bond, $R_1$ is hydrogen, substituted or unsubstituted methyl or substituted or unsubstituted acetyl and $R_2$ is substituted or unsubstituted phenyl or substituted or unsubstituted morpholine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ form, together with the atom to which they are attached, a —C=O group;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_4$ and $R_{4'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein n is 0, 1, 2, 3 or 4, preferably n is 0 or 1; and/or m is 0, 1, 2, 3, 4, 5 or 6; preferably m is 0 or 1, and/or p is 1, 2, 3 or 4; preferably p is 1; and/or X is selected from a bond, and —C($R_x R_{x'}$)—; preferably X is a bond;

and/or $R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, —C(O)$R_6$, —C(O)O$R_6$, —C(O)N$R_6 R_{6'}$ and —S(O)$_2 R_6$; more preferably $R_1$ is hydrogen, substituted or unsubstituted $C_{1-6}$ alkyl or —C(O)$R_6$; wherein the $C_{1-6}$ alkyl is preferably selected from methyl, ethyl, propyl, butyl, pentyl, hexyl, isopropyl, or 2-methylpropyl, more preferably the alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_2$ is selected from substituted or unsubstituted cycloalkyl, substituted or unsubstituted aryl and substituted or unsubstituted heterocyclyl;

wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; more preferably is morpholine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_3$ is selected from hydrogen, halogen, —$R_9$, —O$R_9$, —NO$_2$, —N$R_9 R_{9'''}$, —N$R_9$C(O)$R_{9'}$, —NC(O)O$R_9$, —N$R_9$S(O)$_2 R_{9'}$, —S(O)$_2$N$R_9 R_{9'}$, —N$R_9$C(O)N$R_9 R_{9'}$, —S$R_9$, —S(O)$R_9$, —S(O)$_2 R_9$, —CN, haloalkyl, haloalkoxy, —C(O)O$R_9$, —C(O)N$R_9 R_{9'}$, —N$R_9$S(O)$_2$N$R_{9'} R_{9''}$ and —OC(O)$R_9$; wherein the alkyl is $C_{1-4}$ alkyl like methyl, ethyl, propyl, butyl, pentyl, hexyl, isopropyl, or 2-methylpropyl;

and/or $R_{3'}$, $R_{3''}$ and $R_{3'''}$ are independently selected from hydrogen, halogen, —$R_9$, —NO$_2$, —N$R_9 R_{9'''}$, —N$R_9$C(O)$R_{9'}$, —NC(O)O$R_9$, —N$R_9$S(O)$_2 R_{9'}$, —S(O)$_2$N$R_9 R_{9'}$, —N$R_9$C(O)N$R_{9'} R_{9''}$, —S$R_9$, —S(O)$R_9$, —S(O)$_2 R_9$, —CN, haloalkyl, haloalkoxy, —C(O)O$R_9$, —C(O)N$R_9 R_{9'}$, —N$R_9$S(O)$_2$N$R_{9'} R_{9''}$ and —OC(O)$R_9$;

wherein the alkyl is $C_{1-4}$ alkyl like methyl, ethyl, propyl, butyl, pentyl, hexyl, isopropyl, or 2-methylpropyl;

and/or $R_4$ is selected from hydrogen, —$OR_8$, substituted or unsubstituted $C_{1-6}$ alkyl, substituted or unsubstituted $C_{2-6}$ alkenyl, substituted or unsubstituted $C_{2-6}$ alkynyl, —C(O)$OR_8$, —C(O)$NR_8R_{8'}$, —$NR_8C(O)R_{8'}$, —$NR_8R_{8'''}$ and —NC(O)$OR_8$; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, and substituted or unsubstituted heterocyclyl or substituted or unsubstituted alkyheterocylcyl; wherein the alkyl is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, or 2-methylpropyl, more preferably the alkyl is methyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_7$, $R_{7'}$ and $R_{7''}$ are independently selected from hydrogen, unsubstituted $C_{1-6}$ alkyl, unsubstituted $C_{2-6}$ alkenyl, and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{7'''}$ is selected from hydrogen, unsubstituted $C_{1-6}$ alkyl, unsubstituted $C_{2-6}$ alkenyl, unsubstituted $C_{2-6}$ alkynyl and —Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_8$, $R_{8'}$ and $R_{8''}$ are independently selected from hydrogen, unsubstituted $C_{1-6}$ alkyl, unsubstituted $C_{2-6}$ alkenyl, and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{8'''}$ is selected from hydrogen, unsubstituted $C_{1-6}$ alkyl, unsubstituted $C_{2-6}$ alkenyl, unsubstituted $C_{2-6}$ alkynyl and —Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{9'''}$ is selected from hydrogen, unsubstituted $C_{1-6}$ alkyl, unsubstituted $C_{2-6}$ alkenyl, unsubstituted $C_{2-6}$ alkynyl and —Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{10}$, and $R_{10'}$ are independently selected from hydrogen, unsubstituted $C_{1-6}$ alkyl, unsubstituted $C_{2-6}$ alkenyl, and unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)OR$_7$, —C(O)NR$_7$R$_{7'}$, —NR$_7$C(O)R$_{7'}$, and —NR$_7$R$_{7'''}$; wherein the $C_{1-6}$ alkyl is preferably selected from e methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or $R_{11'''}$ is selected from hydrogen, unsubstituted $C_{1-6}$ alkyl, unsubstituted $C_{2-6}$ alkenyl, unsubstituted $C_{2-6}$ alkynyl and —Boc; wherein the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or

R$_{12}$, R$_{12'}$ and R$_{12''}$ are independently selected from hydrogen, unsubstituted C$_{1-6}$ alkyl, and unsubstituted C$_{2-6}$ alkenyl, unsubstituted C$_{2-6}$ alkynyl; wherein the C$_{1-6}$ alkyl is preferably selected from methyl, ethyl, propyl, butyl, pentyl, hexyl, isopropyl, or 2-methylpropyl;

and/or the C$_{2-6}$-alkenyl is preferably selected from ethylene, propylene, butylene, pentylene, hexylene, isopropylene and isobutylene;

and/or the C$_{2-6}$-alkynyl is preferably selected from ethyne, propyne, butyne, pentyne, hexyne, isopropyne and isobutyne;

and/or

R$_{12'''}$ is selected from hydrogen, unsubstituted C$_{1-6}$ alkyl, unsubstituted C$_{2-6}$ alkenyl, unsubstituted C$_{2-6}$ alkynyl and —Boc; wherein the C$_{1-6}$ alkyl is preferably selected from methyl, ethyl, propyl, butyl, pentyl, hexyl, isopropyl, or 2-methylpropyl;

and/or the C$_{2-6}$-alkenyl is preferably selected from ethylene, propylene, butylene, pentylene, hexylene, isopropylene and isobutylene;

and/or the C$_{2-6}$-alkynyl is preferably selected from ethyne, propyne, butyne, pentyne, hexyne, isopropyne and isobutyne;

and/or

R$_{13}$, R$_{13'}$ and R$_{13''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl; wherein the alkyl is C$_{1-6}$ alkyl like methyl, ethyl, propyl, butyl, pentyl, hexyl, isopropyl, or 2-methylpropyl;

and/or the C$_{1-6}$ alkyl is preferably selected from methyl, ethyl, propyl, butyl, pentyl, hexyl, isopropyl, isobutyl and 2-methylpropyl, and/or the C$_{2-6}$-alkenyl is preferably selected from ethylene, propylene, butylene, pentylene, hexylene, isopropylene and isobutylene;

and/or the C$_{2-6}$-alkynyl is preferably selected from ethyne, propyne, butyne, pentyne, hexyne, isopropyne and isobutyne;

and/or

R$_{13'''}$ is selected from hydrogen, unsubstituted C$_{1-6}$ alkyl, unsubstituted C$_{2-6}$ alkenyl, unsubstituted C$_{2-6}$ alkynyl and —Boc; wherein the C$_{1-6}$ alkyl is preferably selected from methyl, ethyl, propyl, butyl, pentyl, hexyl, isopropyl, or 2-methylpropyl;

and/or the C$_{2-6}$-alkenyl is preferably selected from ethylene, propylene, butylene, pentylene, hexylene, isopropylene and isobutylene;

and/or the C$_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in R$_1$ as defined in any of the embodiments of the present invention, the C$_{1-6}$ alkyl is preferably selected from methyl, ethyl, propyl, butyl, pentyl, hexyl, isopropyl, or 2-methylpropyl, more preferably the alkyl is methyl;

and/or the C$_{2-6}$-alkenyl is preferably selected from ethylene, propylene, butylene, pentylene, hexylene, isopropylene and isobutylene;

and/or the C$_{2-6}$-alkynyl is preferably selected from ethyne, propyne, butyne, pentyne, hexyne, isopropyne and isobutyne;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is C$_{3-8}$ cycloalkyl like cyclopropyl, cyclobutyl, cyclopentyl, cyclohexyl, cycloheptyl, or cyclooctyl; preferably is C$_{3-7}$ cycloalkyl like cyclopropyl, cyclobutyl, cyclopentyl, cyclohexyl, or cycloheptyl; more preferably from C$_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in R$_2$ as defined in any of the embodiments of the present invention, the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; more preferably is morpholine;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{x'}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, the $C_{1-6}$ alkyl is preferably selected from methyl, ethyl, propyl, butyl, pentyl, hexyl, isopropyl, or 2-methylpropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{3'}$, $R_{3''}$ and $R_{3'''}$ as defined in any of the embodiments of the present invention, the $C_{1-6}$ alkyl is preferably selected from methyl, ethyl, propyl, butyl, pentyl, hexyl, isopropyl, or 2-methylpropyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{4'}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{5'}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ as defined in any of the embodiments of the present invention, the alkyl is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, isobutyl and 2-methylpropyl, more preferably the alkyl is methyl and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphtyl, or anthracene; preferably is napthyl and phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{6'}$ as defined in any of the embodiments of the present invention, the alkyl is $C_{1-6}$ alkyl like methyl, ethyl, propyl, butyl, pentyl, hexyl, isopropyl, or 2-methylpropyl;

and/or the $C_{1-6}$ alkyl is preferably selected from methyl, ethyl, propyl, butyl, pentyl, hexyl, isopropyl, isobutyl and 2-methylpropyl, and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphtyl, or anthracene; preferably is napthyl and phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_7$, $R_{7'}$ and $R_{7''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{7'''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$, $R_{8'}$ and $R_{8''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{8'''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$, $R_{9'}$ and $R_{9''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{9'''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10}$ as defined in any of the embodiments of the present invention,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{10'}$ as defined in any of the embodiments of the present invention,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention,
the $C_{1-6}$ alkyl is preferably selected from methyl, ethyl, propyl, butyl, pentyl, hexyl, isopropyl, or 2-methylpropyl;
and/or
the $C_{2-6}$-alkenyl is preferably selected from ethylene, propylene, butylene, pentylene, hexylene, isopropylene and isobutylene;
and/or
the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$, $R_{13'}$ and $R_{13''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

and/or the aryl is selected from phenyl, naphtyl, or anthracene; preferably is napthyl and phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from oxazepan, pyrrolidine, imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13'''}$ as defined in any of the embodiments of the present invention, the $C_{1-6}$ alkyl is preferably selected from methyl, ethyl, propyl, butyl, pentyl, hexyl, isopropyl, or 2-methylpropyl;

and/or the $C_{2-6}$-alkenyl is preferably selected from ethylene, propylene, butylene, pentylene, hexylene, isopropylene and isobutylene;

and/or the $C_{2-6}$-alkynyl is preferably selected from ethyne, propyne, butyne, pentyne, hexyne, isopropyne and isobutyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein n is 0, 1, 2, 3 or 4, preferably n is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0, 1, 2, 3, 4, 5 or 6; preferably m is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 1, 2, 3 or 4; preferably p is 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein X is selected from a bond, and —$C(R_xR_{x'})$—; preferably X is a bond;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 0 or 1; and n is 0 or 1; and p is 1; and $R_1$ is selected from hydrogen, substituted or unsubstituted methyl and substituted or unsubstituted acetyl;

and $R_2$ is selected from substituted or unsubstituted phenyl and substituted or unsubstituted morpholine;

and

X is a bond;

and $R_3$, $R_{3'}$, $R_{3''}$ and $R_{3'''}$ are all hydrogen;

and $R_4$ and $R_{4'}$ are both hydrogen, or may form together with the carbon to which they are attached, a C=O group;

and $R_5$ and $R_{5'}$ are both hydrogen;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment $R_1$ is hydrogen or a substituted or unsubstituted group selected from methyl and acetyl.

In another preferred embodiment $R_1$ is hydrogen or a substituted or unsubstituted methyl.

In a preferred embodiment $R_2$ is a substituted or unsubstituted phenyl or morpholine.

In a preferred embodiment $R_2$ is a substituted or unsubstituted phenyl.

In a preferred embodiment $R_3$ is hydrogen.

In a preferred embodiment $R_{3'}$, $R_{3''}$ and $R_{3'''}$ are all hydrogen.

In a preferred embodiment $R_3$, $R_{3'}$, $R_{3''}$ and $R_{3'''}$ are all hydrogen.

In a preferred embodiment $R_4$ and $R_{4'}$ are both hydrogen.

In a preferred embodiment $R_4$ and $R_{4'}$ form together with the carbon to which they are attached a C=O group.

In a preferred embodiment $R_5$ and $R_{5'}$ are both hydrogen.

In a preferred embodiment $R_6$ is substituted or unsubstituted methyl, preferably unsubstituted methyl.

In a preferred embodiment $R_x$ is hydrogen.

In a preferred embodiment $R_x'$ is hydrogen.

In a preferred embodiment $R_x$ and $R_x'$ are both hydrogen.

In another preferred embodiment n is 0 or 1.

In another preferred embodiment m is 0 or 1.

In another preferred embodiment p is 1.

In another preferred embodiment

X is a bond or —CH$_2$—.

In another preferred embodiment

X is a bond.

In an particular embodiment the halogen is fluorine, chlorine, iodine or bromine.

In an particular embodiment the halogen is fluorine or chlorine.

In a preferred further embodiment, the compounds of the general Formula (I) are selected from

| EX | Chemical name |
|---|---|
| 1 | 1'-phenethyl-2,4-dihydro-1H-spiro[isoquinoline-3,4'-piperidin]-1-one |
| 2 | 1'-benzyl-2,4-dihydro-1H-spiro[isoquinoline-3,4'-piperidin]-1-one |
| 3 | 1'-phenethyl-2,4-dihydro-1H-spiro[isoquinoline-3,4'-piperidine] |
| 4 | 1'-benzyl-2,4-dihydro-1H-spiro[isoquinoline-3,4'-piperidine] |
| 5 | 1-(1'-phenethyl-1H-spiro[isoquinoline-3,4'-piperidine]-2(4H)-yl)-ethanone |
| 6 | 1'-benzyl-2-methyl-2,4-dihydro-1H-spiro[isoquinoline-3,4'-piperidine] |
| 7 | 4-(2-(2-methyl-2,4-dihydro-1H-spiro[isoquinoline-3,4'-piperidine]-1'-yl)ethyl)morpholine | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, p is 1, X is a bond, and $R_2$ is substituted or unsubstituted phenyl; the compound being exemplified in examples 1, 3 and 5;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 1, p is 1, X is a bond, and $R_2$ is substituted or unsubstituted morpholine; the compound being exemplified in examples 7;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I), is a compound wherein n is 0, p is 1, X is a bond, and $R_2$ is substituted or unsubstituted phenyl; the compound being exemplified in examples 2, 4 and 6;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 1, m is 0, p is 1, X is a bond and $R_1$ is hydrogen, substituted or unsubstituted methyl or substituted or unsubstituted acetyl; the compound being exemplified in examples 1, 3, 5 and 7;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 0, m is 0, p is 1, X is a bond and $R_1$ is hydrogen or substituted or unsubstituted methyl; the compound being exemplified in examples 2, 4 and 6;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 1, m is 0, p is 1, X is a bond, and $R_1$ is —C(O)$R_6$, wherein $R_6$ is substituted or unsubstituted methyl; the compound being exemplified in examples 5;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein n is 1, m is 0, p is 1, X is a bond, $R_1$ is hydrogen, substituted or unsubstituted methyl or substituted or unsubstituted acetyl and $R_2$ is substituted or unsubstituted phenyl or substituted or unsubstituted morpholine; the compound being exemplified in examples 1, 3, 5 and 7;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein $R_4$ and $R_{4'}$ form, together with the atom to which they are attached, a —C=O group, the compound being exemplified in examples 1 and 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment, the compound according to the invention of general Formula (I) is a compound wherein $R_4$ and $R_{4'}$ are both hydrogen, the compound being exemplified in examples 3 to 7;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, —C(O)$R_6$, —C(O)O$R_6$, —C(O)N$R_6R_{6'}$, and —S(O)$_2R_6$;

wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, and substituted or unsubstituted heterocyclyl or substituted or unsubstituted alkyheterocylcyl;

wherein said cycloalkyl, aryl or heterocyclyl in $R_1$ or $R_6$, also in alkylaryl, alkylcycloalkyl and alkylheterocyclyl, if substituted, is substituted with one or more substituent/s selected from halogen, —$R_{11}$, —O$R_{11}$, —NO$_2$, —N$R_{11}R_{11'''}$, N$R_{11}$C(O)$R_{11'}$, —N$R_{11}$S(O)$_2R_{11'}$, —S(O)$_2$N$R_{11}R_{11'}$, —N$R_{11}$C(O)N$R_{11'}R_{11''}$, —S$R_{11}$, —S(O)$R_{11}$, S(O)$_2R_{11}$, —CN, haloalkyl, haloalkoxy, —C(O)O$R_{11}$, —C(O)N$R_{11}R_{11'}$, — and —N$R_{11}$S(O)$_2$N$R_{11'}R_{11''}$;

wherein, said cycloalkyl or non-aromatic heterocyclyl in $R_1$ or $R_6$, also in alkylcycloalkyl and alkylheterocyclyl, if substituted, may also be substituted with

or =O;

wherein the alkyl, alkenyl or alkynyl in $R_1$ or $R_6$, if substituted, is substituted with one or more substituent/s selected from —O$R_{11}$, halogen, —CN, haloalkyl, haloalkoxy, —S$R_{11}$, —S(O)$R_{11}$, and —S(O)$_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), $R_2$ is selected from substituted or unsubstituted cycloalkyl, substituted or unsubstituted aryl and substituted or unsubstituted heterocyclyl;

wherein said cycloalkyl, aryl or heterocyclyl in $R_2$, if substituted, is substituted with one or more substituent/s selected from halogen, —$R_{12}$, —O$R_{12}$, —NO$_2$, —N$R_{12}R_{12'''}$, N$R_{12}$C(O)$R_{12'}$, —S(O)$_2$N$R_{12}R_{12'}$, —N$R_{12}$C(O)N$R_{12'}R_{12''}$, —S$R_{12}$, —S(O)$R_{12}$, S(O)$_2R_{12}$, —CN, haloalkyl, haloalkoxy, —C(O)O$R_{12}$, —C(O)N$R_{12}R_{12'}$, and —N$R_{12}$S(O)$_2$N$R_{12'}R_{12''}$;

wherein, said cycloalkyl or non-aromatic heterocyclyl in $R_2$, if substituted, may also be substituted with

or =O;

wherein the alkyl, alkenyl or alkynyl in $R_2$, if substituted, is substituted with one or more substituent/s selected from —OR$_{12}$, halogen, —CN, haloalkyl, haloalkoxy, —SR$_{12}$, —S(O)R$_{12}$, and —S(O)$_2$R$_{12}$;

wherein R$_{12}$, R$_{12'}$ and R$_{12''}$ are independently selected from hydrogen, unsubstituted C$_{1-6}$ alkyl, and unsubstituted C$_{2-6}$ alkenyl, unsubstituted C$_{2-6}$ alkynyl;

and wherein R$_{12'''}$ is selected from hydrogen, unsubstituted C$_{1-6}$ alkyl, unsubstituted C$_{2-6}$ alkenyl, unsubstituted C$_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the alkyl, alkenyl or alkynyl, other than those defined in R$_1$, R$_2$ or R$_6$, if substituted, is substituted with one or more substituent/s selected from —OR$_{10}$, halogen, —CN, haloalkyl, haloalkoxy, —SR$_{10}$, —S(O)R$_{10}$, and —S(O)$_2$R$_{10}$;

wherein R$_{10}$, and R$_{10'}$ are independently selected from hydrogen, unsubstituted C$_{1-6}$ alkyl, unsubstituted C$_{2-6}$ alkenyl, and unsubstituted C$_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl, also in alkylaryl, alkylcycloalkyl and alkylheterocyclyl, other than those defined in R$_1$, R$_2$ or R$_6$, if substituted, is substituted with one or more substituent/s selected from halogen, —R$_{13}$, —OR$_{13}$, —NO$_2$, —NR$_{13}$R$_{13'''}$, NR$_{13}$C(O)R$_{13'}$, —NR$_{13}$S(O)$_2$R__', —S(O)$_2$NR$_{13}$R$_{13'}$, —NR$_{13}$C(O)NR$_{13'}$R$_{13''}$, —SR$_{13}$, —S(O)R$_{13}$, S(O)$_2$R$_{13}$, —CN, haloalkyl, haloalkoxy, —C(O)OR$_{13}$, —C(O)NR$_{13}$R$_{13'}$, —OCH$_2$CH$_2$OH, —NR$_{13}$S(O)$_2$NR$_{13'}$R$_{13''}$ and C(CH$_3$)$_2$OR$_{13}$;

wherein cycloalkyl or non-aromatic heterocyclyl, other than those defined in R$_1$, R$_2$ or R$_6$, also in alkylcycloalkyl and alkylheterocyclyl, if substituted, may also be substituted with

or ═O;

wherein R$_{13}$, R$_{13'}$ and R$_{13''}$ are independently selected from hydrogen, unsubstituted C$_{1-6}$ alkyl, unsubstituted C$_{2-6}$ alkenyl, unsubstituted C$_{2-6}$ alkynyl, unsubstituted aryl, unsubstituted alkylaryl, unsubstituted cycloalkyl and unsubstituted alkylcycloalkyl, unsubstituted heterocyclyl and unsubstituted alkyheterocylcyl;

and wherein R$_{13'''}$ is selected from hydrogen, unsubstituted C$_{1-6}$ alkyl, unsubstituted C$_{2-6}$ alkenyl, unsubstituted C$_{2-6}$ alkynyl and —Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to R$_1$ of any of the embodiments of the present invention, the cycloalkyl, aryl or heterocyclyl in R$_1$, if substituted, is substituted with one or more substituent/s selected from halogen, —R$_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, — and —NR$_{11}$S(O)$_2$NR$_{11'}$R$_{11''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to R$_6$ of any of the embodiments of the present invention, the cycloalkyl, aryl or heterocyclyl in R$_6$, also in alkylaryl, alkylcycloalkyl and alkylheterocyclyl, if substituted, is substituted with one or more substituent/s selected from halogen, —R$_{11}$, —OR$_{11}$, —NO$_2$, —NR$_{11}$R$_{11'''}$, NR$_{11}$C(O)R$_{11'}$, —NR$_{11}$S(O)$_2$R$_{11'}$, —S(O)$_2$NR$_{11}$R$_{11'}$, —NR$_{11}$C(O)NR$_{11'}$R$_{11''}$, —SR$_{11}$, —S(O)R$_{11}$, S(O)$_2$R$_{11}$, —CN, haloalkyl, haloalkoxy, —C(O)OR$_{11}$, —C(O)NR$_{11}$R$_{11'}$, — and —NR$_{11}$S(O)$_2$NR$_{11'}$R$_{11''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to R$_1$ of any of the embodiments of the present invention, the cycloalkyl or non-aromatic heterocyclyl in R$_1$, if substituted, may also be substituted with

or ═O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to R$_6$ of any of the embodiments of the present invention, the cycloalkyl or non-aromatic heterocyclyl in R$_6$, also in alkylcycloalkyl and non-aromatic alkylheterocyclyl, if substituted, may also be substituted with

or ═O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl, aryl or heterocyclyl in $R_2$, if substituted, is substituted with one or more substituent/s selected from halogen, $-R_{12}$, $-OR_{12}$, $-NO_2$, $-NR_{12}R_{12'''}$, $NR_{12}C(O)R_{12'}$, $-S(O)_2NR_{12}R_{12'}$, $-NR_{12}C(O)NR_{12'}R_{12''}$, $-SR_{12}$, $-S(O)R_{12}$, $S(O)_2R_{12}$, $-CN$, haloalkyl, haloalkoxy, $-C(O)OR_{12}$, $-C(O)NR_{12}R_{12'}$, and $-NR_{12}S(O)_2NR_{12'}R_{12''}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl or non-aromatic heterocyclyl in $R_2$, if substituted, may also be substituted with

or $=O$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_1$, $R_2$ or $R_6$ of any of the embodiments of the present invention, the alkyl, alkenyl or alkynyl, other than those defined in $R_1$, $R_2$ or $R_6$, if substituted, is substituted with one or more substituent/s selected from $-OR_{10}$, halogen, $-CN$, haloalkyl, haloalkoxy, $-SR_{10}$, $-S(O)R_{10}$, and $-S(O)_2R_{10}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$, $R_2$ or $R_6$ of any of the embodiments of the present invention, the aryl, heterocyclyl or cycloalkyl, also in alkylaryl, alkylcycloalkyl and alkylheterocyclyl, other than those defined in $R_1$, $R_2$ or $R_6$, if substituted, is substituted with one or more substituent/s selected from halogen, $-R_{13}$, $-OR_{13}$, $-NO_2$, $-NR_{13}R_{13'''}$, $NR_{13}C(O)R_{13'}$, $-NR_{13}S(O)_2R_{13'}$, $-S(O)_2NR_{13}R_{13'}$, $-NR_{13}C(O)NR_{13'}R_{13''}$, $-SR_{13}$, $-S(O)R_{13}$, $S(O)_2R_{13}$, $-CN$, haloalkyl, haloalkoxy, $-C(O)OR_{13}$, $-C(O)NR_{13}R_{13'}$, $-OCH_2CH_2OH$, $-NR_{13}S(O)_2NR_{13'}R_{13''}$ and $C(CH_3)_2OR_{13}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_1$, $R_2$ or $R_6$ of any of the embodiments of the present invention, the cycloalkyl or non-aromatic heterocyclyl, other than those defined in $R_1$, $R_2$ or $R_6$, also in alkylcycloalkyl and alkylheterocyclyl, if substituted, may also be substituted with

or $=O$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the halogen is fluorine, chlorine, iodine or bromine;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a most preferred embodiment of the compound according to the invention of general Formula (I)

the halogen is fluorine or chlorine optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I), the haloalkyl is $-CF3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the compound according to the invention of general Formula (I), the haloalkoxy is $-OCF3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as ligands of the $\sigma_1$ receptor it is a very preferred embodiment in which the compounds are selected which act as ligands of the $\sigma_1$ receptor and especially compounds which have a binding expressed as $K_i$ which is preferably <1000 nM, more preferably <500 nM, even more preferably <100 nM.

In the following the phrase "compound of the invention" is used. This is to be understood as any compound according to the invention as described above according to general Formula (I), (I'), ($I^{2'}$), ($I^{3'}$) or ($I^{4'}$)

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to Formula (I), following scheme 1.

A preferred embodiment of the invention is a process for the production of a compound according to Formula (I), wherein m, n, p, $R_1$, $R_2$, $R_3$, $R_{3'}$, $R_{3''}$, $R_{3'''}$, $R_4$, $R_{4'}$, $R_5$, $R_{5'}$ and X have the meanings defined in the description.

In a particular embodiment there is a process for the production of a compound according to Formula (I),

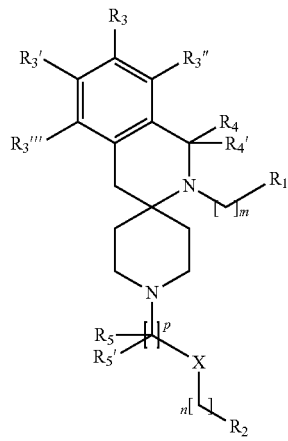
(I)

said process comprises reacting a compound of Formula (Ib')

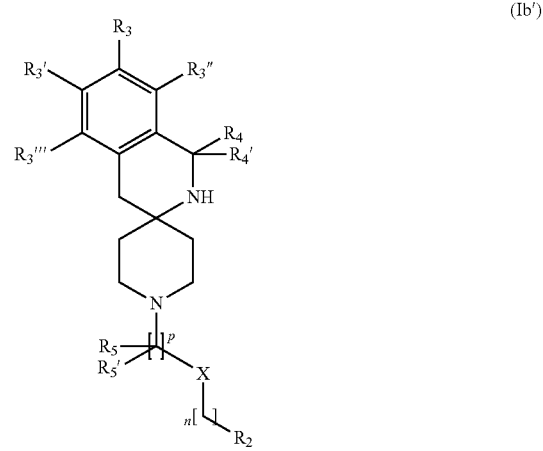
(Ib')

with a compound of Formula (XIa) in an alkylating reaction, (XIb) in a reductive amination reaction, (XIc) in an acylation reaction or (XId) in an acylation reaction

XIa

XIb

XIc

XId following the operative conditions as described in STEP 7 of scheme 1, wherein L, W, m, n, p, $R_1$, $R_2$, $R_3$, $R_{3'}$, $R_{3''}$, $R_{3'''}$, $R_4$, $R_{4'}$, $R_5$, $R_{5'}$, $R_6$ and X have the meaning as defined in the description and in scheme 1.

In a particular embodiment the production of a compound according to Formula (I), wherein $R_4$ and $R_{4'}$ are hydrogen,

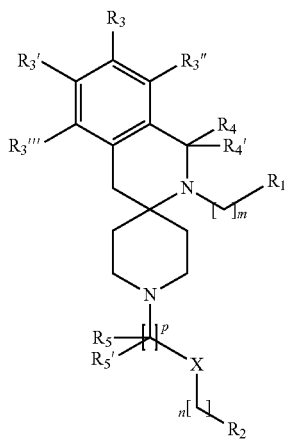

comprises reacting a compound of Formula (Ib)

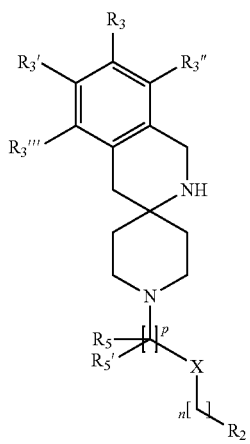

with a compound of Formula (XIa) in an alkylating reaction, (XIb) in a reductive amination reaction, (XIc) in an acylation reaction or (XId) in an acylation reaction

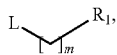
XIa

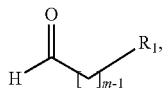
XIb

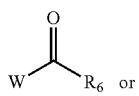
XIc

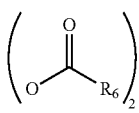
XId following the operative conditions as described in STEP 7 of scheme 1, wherein L, W, m, n, p, $R_1$, $R_2$, $R_3$, $R_3'$, $R_3''$, $R_3'''$, $R_5$, $R_5'$, $R_6$ and X have the meaning as defined in the description and in scheme 1.

In a particular embodiment the production of a compound according to Formula (I), wherein $R_4$ and $R_4'$ form a C=O group,

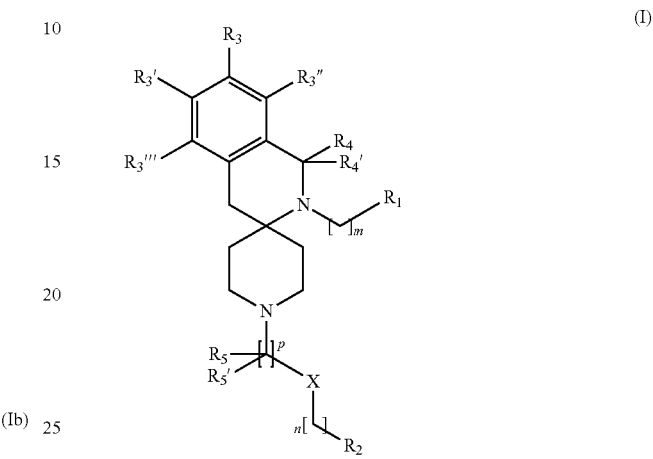
(I)

comprises reacting a compound of Formula (Ia)

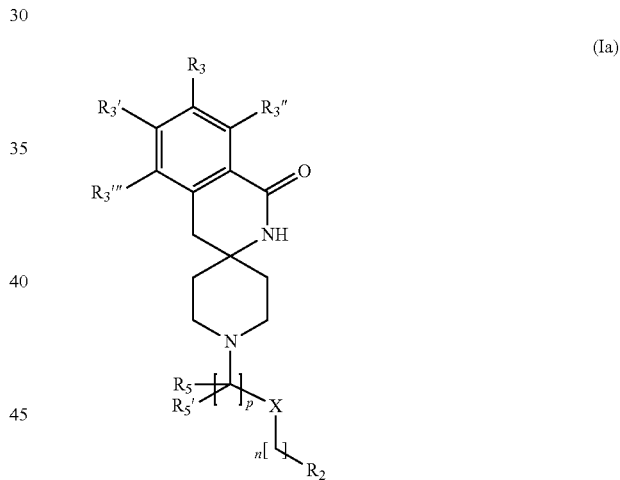
(Ia)

with a compound of Formula (XIa) in an alkylating reaction, (XIc) in an acylation reaction or (XId) in an acylation reaction XIa XIc

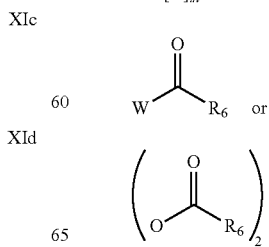
XId following the operative conditions as described in STEP 7 of scheme 1, wherein L, W, m, n, p, $R_1$, $R_2$, $R_3$, $R_3'$, $R_3''$, $R_3'''$, $R_5$, $R_5'$, $R_6$ and X have the meaning as defined in the description and in scheme 1.

In a particular embodiment there is a process for the production of a compound according to Formula (X') or (Ic'),

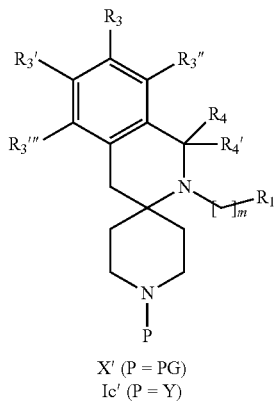

X' (P = PG)
Ic' (P = Y)

said process comprises reacting a compound of Formula (IX') or (Ib')

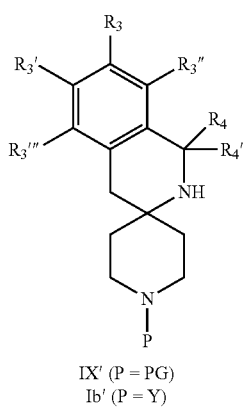

IX' (P = PG)
Ib' (P = Y)

with a compound of Formula (XIa) in an alkylating reaction, (XIb) in a reductive amination reaction, (XIc) in an acylation reaction or (XId) in an acylation reaction

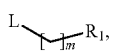

XIa

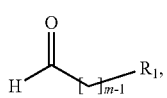

XIb

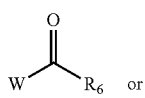

XIc

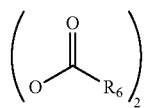

XId following the operative conditions as described in STEP 7 of scheme 1, wherein PG, Y, L, W, m, $R_1$, $R_3$, $R_3'$, $R_3''$, $R_3'''$, $R_4$, $R_4'$, and $R_6$ have the meaning as defined in the description and in scheme 1.

In a particular embodiment there is a process for the production of a compound according to Formula (I),

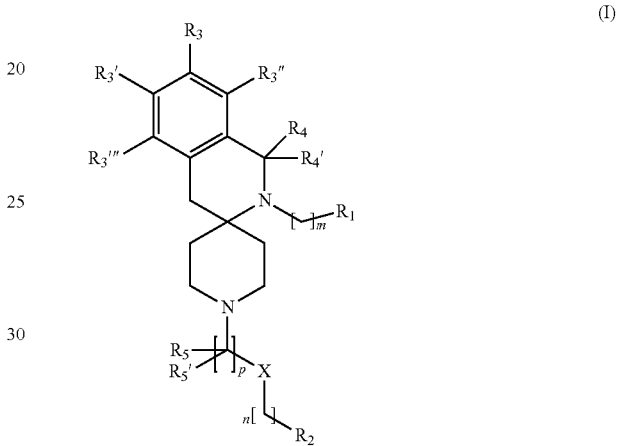

(I)

said process comprises reacting a compound of Formula (XVII')

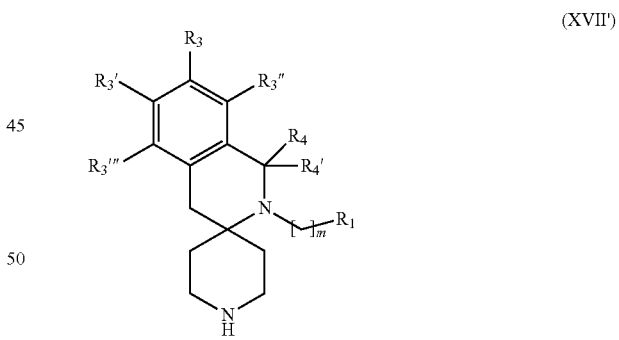

(XVII')

with a compound of Formula (XIIIa) in an alkylation reaction or (XIIIb) in a reductive amination reaction

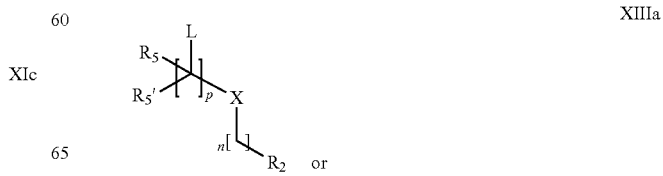

XIIIa or

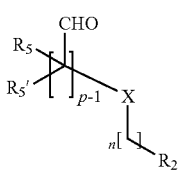

following the operative conditions as described in the general part of scheme 1, wherein L, m, n, p, $R_1$, $R_2$, $R_3$, $R_3'$, $R_3''$, $R_3'''$, $R_4$, $R_4'$, $R_5$, $R_5'$ and X have the meaning as defined in the description and in scheme 1.

In a particular embodiment there is a process for the production of a compound according to Formula (X) or (Ic),

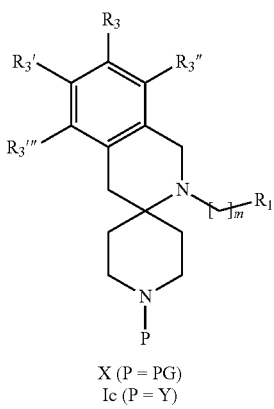

X (P = PG)
Ic (P = Y)

said process comprises reacting a compound of Formula (IX) or (Ib) respectively,

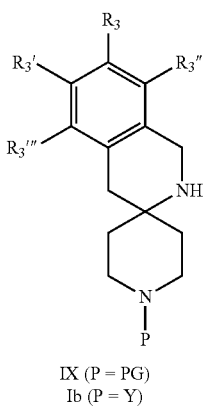

IX (P = PG)
Ib (P = Y)

with a compound of Formula (XIa) in an alkylating reaction, (XIb) in a reductive amination reaction, (XIc) in an acylation reaction or (XId) in an acylation reaction

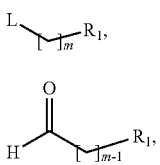

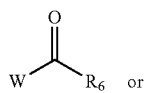

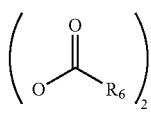

following the operative conditions as described in STEP 7 of scheme 1, wherein PG, Y, L, W, m, $R_1$, $R_3$, $R_3'$, $R_3''$, $R_3'''$ and $R_6$ have the meaning as defined in the description and in scheme 1.

In a particular embodiment there is a process for the production of a compound according to Formula (IX) or (Ib),

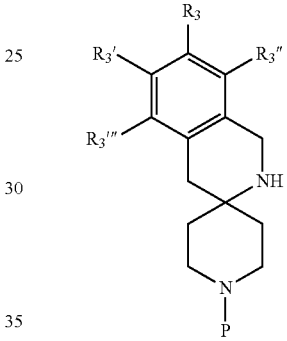

IX (P = PG)
Ib (P = Y)

said process comprises a reduction of a compound of Formula (VIII) or (Ia) respectively,

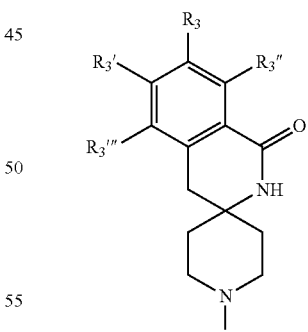

VIII (P = PG)
Ia (P = Y)

following the operative conditions as described in STEP 6 of scheme 1, wherein PG, Y, $R_1$, $R_3$, $R_3'$, $R_3''$ and $R_3'''$ have the meaning as defined in the description and in scheme 1.

In a particular embodiment there is a process for the production of a compound according to Formula (VIII) or (Ia)

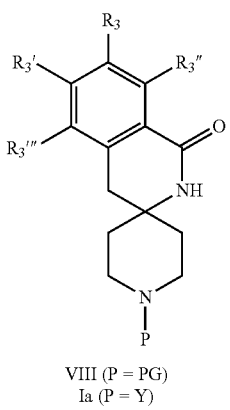

VIII (P = PG)
Ia (P = Y)

said process comprises a rearrangement reaction of a compound of Formula (VIIa) or (VIIb), respectively

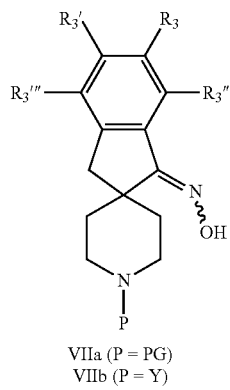

VIIa (P = PG)
VIIb (P = Y)

following the operative conditions as described in STEP 5 of scheme 1, wherein PG, Y, $R_1$, $R_3$, $R_{3'}$, $R_{3''}$ and $R_{3'''}$ have the meaning as defined in the description and in scheme 1.

In a particular embodiment there is a process for the production of a compound according to Formula (VIIa) or (VIIb)

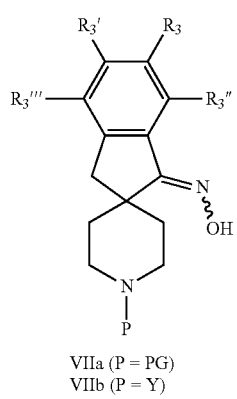

VIIa (P = PG)
VIIb (P = Y)

said process comprises reacting a compound of Formula (VIa) or (VIb) respectively,

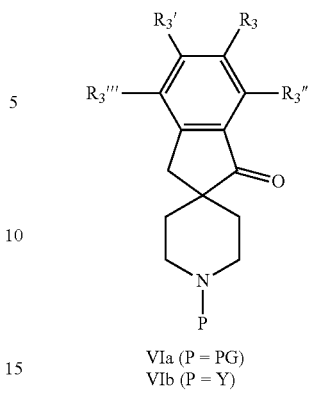

VIa (P = PG)
VIb (P = Y)

with hydroxylamine following the operative conditions as described in STEP 4 of scheme 1,
wherein PG, Y, $R_3$, $R_{3'}$, $R_{3''}$ and $R_{3'''}$ have the meaning as defined in the description and in scheme 1.

In a particular embodiment there is a process for the production of a compound according to Formula (VIa) or (VIb)

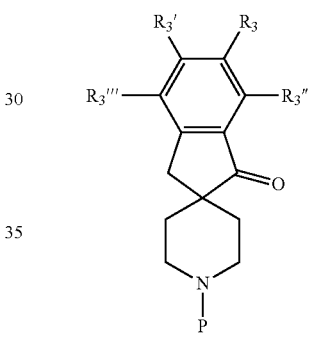

VIa (P = PG)
VIb (P = Y)

said process comprises the cyclization of a compound of Formula (Va) or (Vb) respectively,

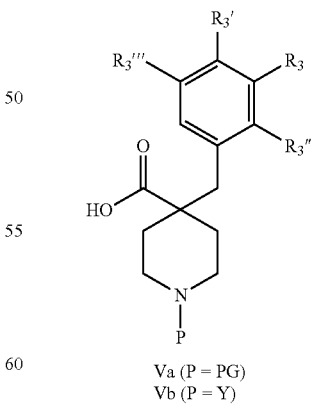

Va (P = PG)
Vb (P = Y)

following the operative conditions as described in STEP 3 of scheme 1,
wherein PG, Y, $R_3$, $R_{3'}$, $R_{3''}$ and $R_{3'''}$ have the meaning as defined above in the description and in scheme 1.

In a particular embodiment there is a process for the production of a compound according to Formula (Va) or (Vb)

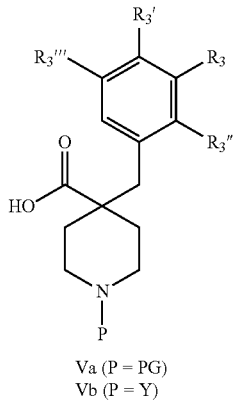

Va (P = PG)
Vb (P = Y)

said process comprises the ester hydrolysis of a compound of Formula (IVa) or (IVb) respectively,

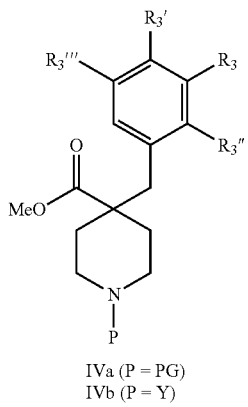

IVa (P = PG)
IVb (P = Y)

following the operative conditions as described in STEP 2 of scheme 1,
wherein PG, Y, $R_3$, $R_{3'}$, $R_{3''}$ and $R_{3'''}$ have the meaning as defined above in the description and in scheme 1.

In a particular embodiment there is a process for the production of a compound according to Formula (IVa) or (IVb)

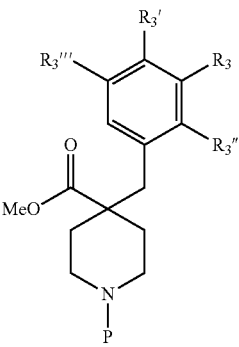

IVa (P = PG)
IVb (P = Y)

said process comprises reacting a compound of Formula (IIa) or (IIb) respectively,

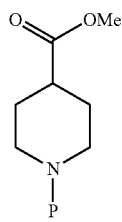

IIa (P = PG)
IIb (P = Y)

with a compound of Formula (III)

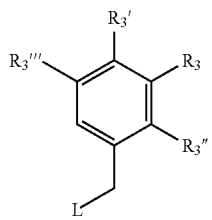

III following the operative conditions as described in STEP 1 of scheme 1,
wherein PG, Y, L, $R_3$, $R_{3'}$, $R_{3''}$ and $R_{3'''}$ have the meaning as defined above in the description and in scheme 1.

In a particular embodiment a compound of Formula (IIa) or (IIb),

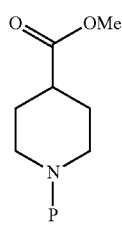

IIa (P = PG)
IIb (P = Y)

wherein PG and Y have the meaning as defined above in the description and in scheme 1, is used for the preparation of compounds of Formula (I).

In a particular embodiment a compound of Formula (III),

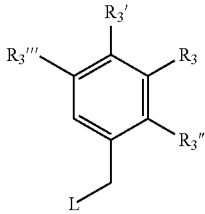

III wherein L, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (IVa) or (IVb),

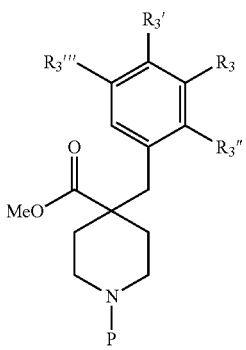

IVa (P = PG)
IVb (P = Y)

wherein PG, Y, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (Va) or (Vb),

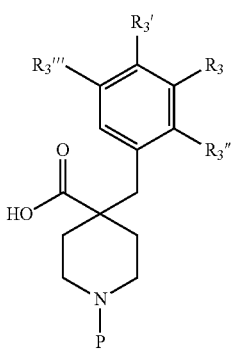

Va (P = PG)
Vb (P = Y)

wherein PG, Y, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (VIa) or (VIb),

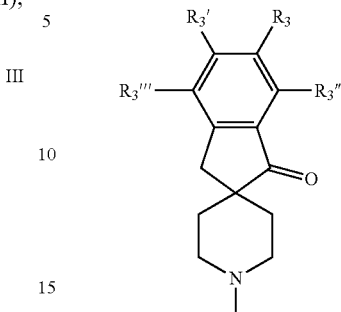

VIa (P = PG)
VIb (P = Y)

wherein PG, Y, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (VIIa) or (VIIb),

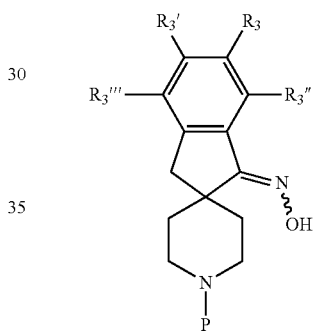

VIIa (P = PG)
VIIb (P = Y)

wherein PG, Y, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (VIII) or (Ia),

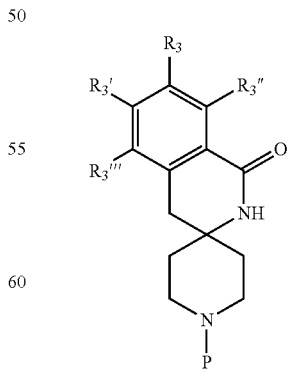

VIII (P = PG)
Ia (P = Y)

wherein PG, Y, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (IX) or (Ib),

IX (P = PG)
Ib (P = Y)

wherein PG, Y, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (X) or (Ic),

X (P = PG)
Ic (P = Y)

wherein m, PG, Y, $R_1$, $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (XIa),

XIa wherein m, L and $R_1$ have the meaning as defined above in the description and in scheme 1, is used for the preparation of compounds of Formula (I).

In a particular embodiment a compound of Formula (XIb),

XIb wherein m and $R_1$ have the meaning as defined above in the description and in scheme 1, is used for the preparation of compounds of Formula (I).

In a particular embodiment a compound of Formula (XIc),

XIc wherein W and $R_6$ have the meaning as defined above in the description and in scheme 1, is used for the preparation of compounds of Formula (I).

In a particular embodiment a compound of Formula (XId),

XId wherein W and $R_6$ have the meaning as defined above in the description and in scheme 1, is used for the preparation of compounds of Formula (I).

In a particular embodiment a compound of Formula (XII),

XII wherein $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (XIIIa),

XIIIa wherein n, p, X, L, $R_2$, $R_5$ and $R_{5'}$ have the meaning as defined above in the description and in scheme 1, is used for the preparation of compounds of Formula (I).

In a particular embodiment a compound of Formula (XIIIb),

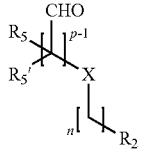

XIIIb wherein n, p, X, Y, $R_2$, $R_5$ and $R_{5'}$ have the meaning as defined above in the description and in scheme 1, is used for the preparation of compounds of Formula (I).

In a particular embodiment a compound of Formula (XIV),

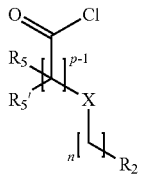

XIV wherein n, p, X, Y, $R_2$, $R_5$ and $R_{5'}$ have the meaning as defined above in the description and in scheme 1, is used for the preparation of compounds of Formula (I).

In a particular embodiment a compound of Formula (XV),

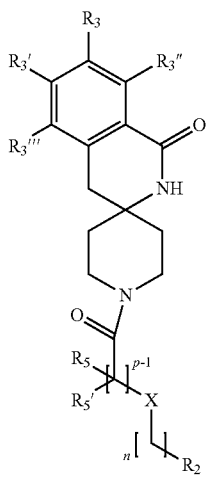

XV wherein n, p, X, $R_2$, $R_3$, $R_{3'}$, $R_{3''}$, $R_{3'''}$, $R_5$ and $R_{5'}$ have the meaning as defined above in the description and in scheme 1, is used for the preparation of compounds of Formula (I).

In a particular embodiment a compound of Formula (XVI),

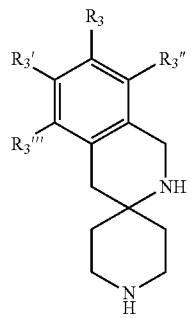

XVI wherein $R_3$, $R_{3'}$, $R_{3''}$ and $R_{3'''}$ have the meaning as defined above in the description and in scheme 1, is used for the preparation of compounds of Formula (I).

In a particular embodiment a compound of Formula (XVII),

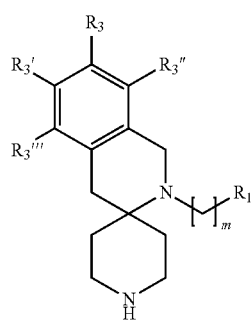

XVII wherein m, $R_1$, $R_3$, $R_{3'}$, $R_{3''}$ and $R_{3'''}$ have the meaning as defined above in the description and in scheme 1, is used for the preparation of compounds of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to the use of a compound of the invention or a pharmaceutically acceptable salt or isomer thereof in the manufacture of a medicament for the treatment of a sigma-1 ($\sigma_1$) receptors related disease.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A process is described in Scheme 1 for the preparation of compounds of general formula I, wherein p, m, n, $R_1$, $R_2$, $R_3$, $R_{3'}$, $R_{3''}$, $R_{3'''}$, $R_4$, $R_{4'}$, $R_5$, $R_{5'}$, and X have the meanings defined above.

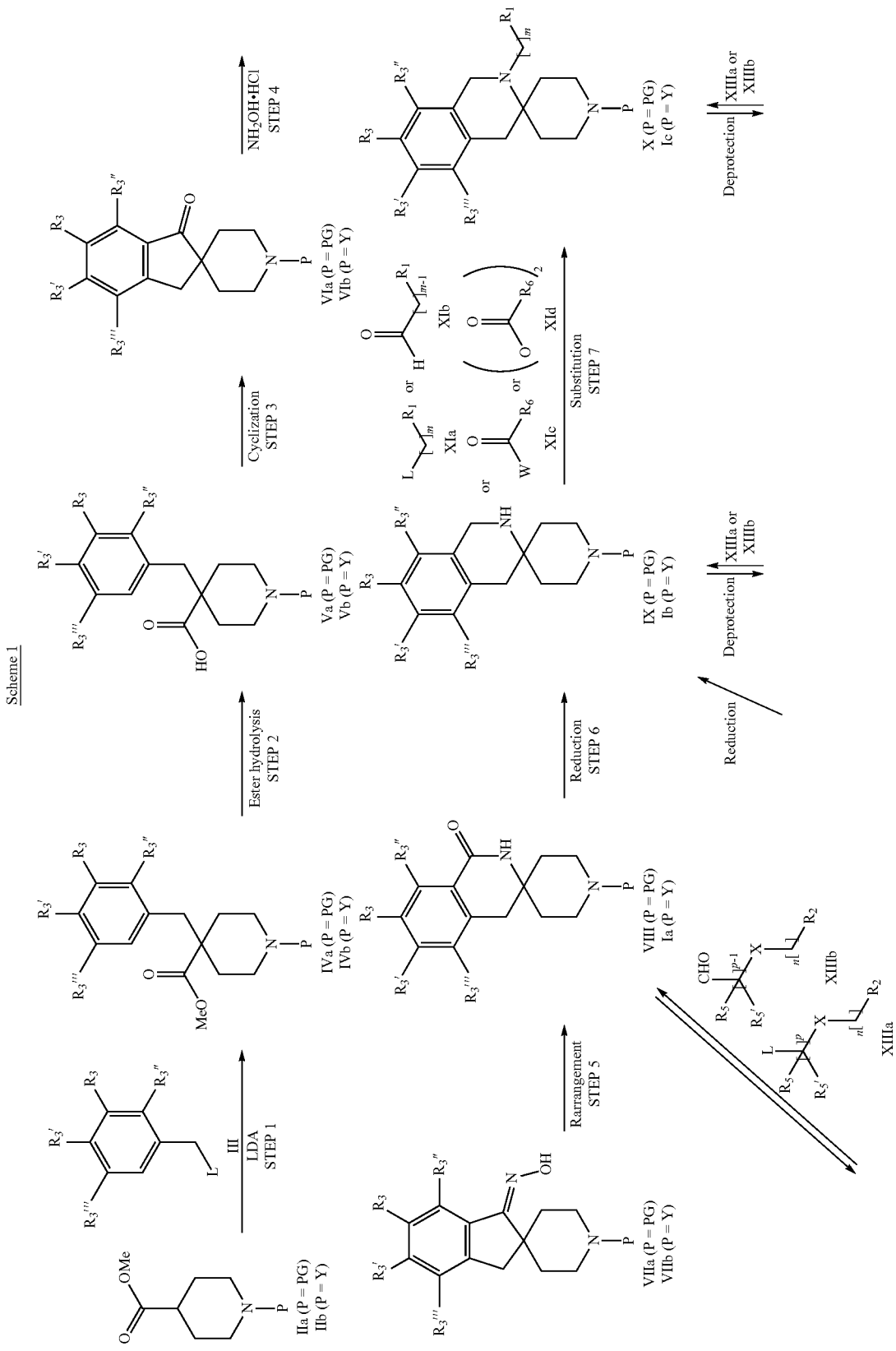

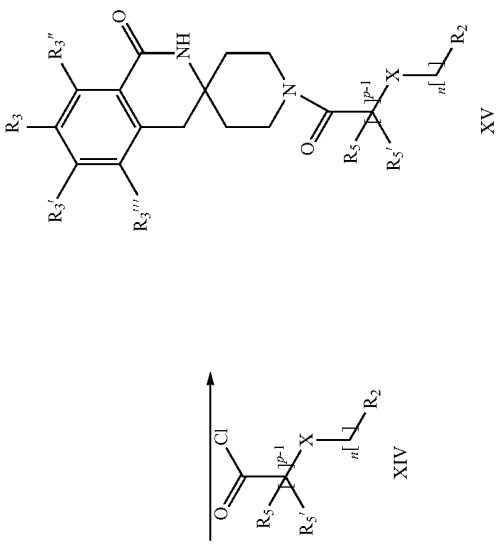
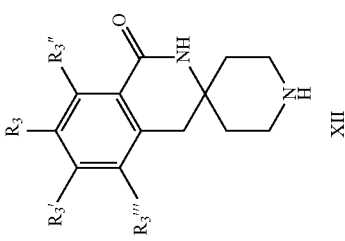
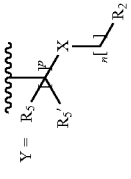
PG = Protecting group

Where, L is a leaving group such as chloro, bromo, mesylate or toxylate and W is chloro, bromo, —OH, —O-methyl (—OMe) or —O-ethyl (—OEt), Y is the group indicated in Scheme 1 and PG is a protecting group.

This process is carried out as described below:

Step 1: A compound of formula IVa or IVb is prepared by treating a piperidine of formula IIa or IIb with a strong base such as LDA in a suitable solvent such as THF, at a suitable temperature comprised between −78° C. and 0° C., preferably at −5° C. and subsequently treating the resulting deprotonated intermediate with a compound of formula III at a suitable temperature comprised between −5° C. and room temperature, preferably at room temperature.

Step 2: The hydrolysis of the ester moiety in a compound of formula IVa or IVb renders a compound of general formula Va or Vb. This reaction can be carried out in the presence of an acid, such as aqueous HCl at a suitable temperature comprised between room temperature and the reflux temperature, preferably at reflux temperature.

Step 3: The intramolecular Friedel-Crafts reaction of a compound of formula Va or Vb renders a compound of formula VIa or VIb. The cyclization reaction is carried out in the presence of an acid, such as polyphosphoric acid and at a suitable temperature, comprised between 50° C. and 130° C., preferably at 130° C.

Step 4: Oxime derivatives of formula VIIa or VIIb are prepared by treating compounds of formula VIa or VIb with hydroxylamine, in a suitable solvent such as water or alcohols, preferably in ethanol, in the presence of a base such as pyridine and at a suitable temperature, preferably at the reflux temperature.

Step 5: The Beckman rearrangement of oximes of formula VIIa or VIIb renders amide compounds of formula VIII or Ia. This reaction can be carried out in the presence of an acid, such as acetic acid, hydrochloric acid, polyphosphoric acid or sulphuric acid, preferably polyphosphoric acid, at a suitable temperature, comprised between 50° C. and 130° C., preferably at 130° C.

Step 6: Compounds of general formula IX or Ib are prepared, respectively, by reduction of lactam compounds of formula VIII or Ia with a suitable agent such as borane, in a suitable solvent such as toluene, at a suitable temperature comprised between room temperature and the reflux temperature, preferably at reflux temperature. Other alternative reducing agents can be used, such as lithium aluminium hydride in a suitable solvent such as THF, at a suitable temperature comprised between room temperature and reflux temperature, preferably at room temperature.

Step 7: Compounds of general formula X or Ic are prepared by substitution of the NH group of compounds IX or Ib, respectively, with appropriate methods. Thus the alkylation of IX or Ib with a compound of formula XIa is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, the reactions can be carried out in a microwave reactor. Additionally, an activating agent such as NaI can be used.

The reductive amination of a compound of formula IX or Ib with a compound of formula XIb, is carried out in the presence of a reductive reagent, preferably sodium triacetoxyborohydride, in a suitable solvent, preferably methanol, at a suitable temperature comprised between room temperature and the reflux temperature, preferably at room temperature.

The acylation reaction of a compound of formula IX or Ib with a compound of formula XIc or XId can be effected in different conditions depending on the acid reagent nature. Preferably, the reaction is carried out with an acid anhydride XId, in the presence of a suitable solvent, such as acetonitrile, dichloromethane, 1,4-dioxane or dimethylformamide, preferably in dichloromethane; in the presence of an organic base such as triethylamine, pyridine or diisopropylethylamine, preferably pyridine; at a suitable temperature comprised between room temperature and the reflux temperature, preferably at reflux temperature.

The process described by Steps 1 to 7 represents the general route for the preparation of compounds of formula I. Additionally, the functional groups present in any of the positions can be interconverted using reactions known to those skilled in the art.

Among these transformations, the protecting groups of the different intermediates can be deprotected at any step and subsequently substituted to provide variations in the group P. Thus, compounds VIII can be deprotected to provide compounds XII, compounds IX to provide compounds XVI and compounds X to provide compounds XVII. If the protecting group is benzyl the deprotection is carried out with hydrogen at a pressure comprised between 1 and 10 bar, in a suitable solvent such as methanol or ethanol, optionally in the presence of an acid such as acetic or hydrochloric acid, at a suitable temperature comprised between room temperature and the reflux temperature, preferably at room temperature. The unprotected derivatives XVI can also be obtained by reduction of intermediates XII using the same conditions described above for the reduction of VIII.

From deprotected compounds of general formula XII, XVI and XVII, compounds of general formula Ia, b, c can be respectively prepared by reaction with suitable reagents, such as those of formula XIIIa-b, using different conditions depending on the reagent nature. Thus:

The alkylation reaction with a compound of formula XIIIa is carried out in a suitable solvent, such as acetonitrile, dichloromethane, 1,4-dioxane or dimethylformamide, preferably in acetonitrile; in the presence of an inorganic base such as $K_2CO_3$ or $Cs_2CO_3$, or an organic base such as triethylamine or diisopropylethylamine, preferably $K_2CO_3$; at a suitable temperature comprised between room temperature and the reflux temperature, preferably heating, or alternatively, this reaction can be carried out in a microwave reactor. Additionally, an activating agent such as NaI can be used.

The reductive amination with a compound of formula XIIIb, is carried out in the presence of a reductive reagent, preferably sodium triacetoxyborohydride, in an aprotic solvent, preferably tetrahydrofuran or dichloroethane, at a suitable temperature comprised between room temperature and the reflux temperature, preferably in a microwave reactor.

Alternatively, the transformation of a deprotected compound of formula XII, XVI and XVII to a compound of formula Ia-c, can be effected in a two step procedure, involving acylation with an acid chloride of formula XIV following by reduction, as illustrated by the transformation of compound XII to give a compound of formula Ib. The acylation reaction of XII to give XV can be carried out using DIPEA in a suitable solvent such as dichloromethane at a suitable temperature, preferably room temperature. The reduction reaction of XV to give IIb can be effected with a reducing agent such as lithium aluminium hydride, in a suitable solvent such as tetrahydrofuran, at a suitable temperature comprised between 0° C. and room temperature, preferably at 0° C.

Examples

Intermediates and Examples

The following abbreviations are used in the examples:
ACN: acetonitrile
anh: anhydrous
DCM: dichloromethane
EtOH: ethanol
EX: example
h: hour/s
HPLC: high performance liquid chromatography
MeOH: methanol
MS: mass spectrometry
Min.: minutes
Ret.: retention
r.t.: room temperature
THF: tetrahydrofuran The following methods were used to determine the HPLC-MS spectra:

A: Column XBridge C18 5 μm, 2.1×50 mm; flow rate: 0.3 mL/min; A: $CH_3CN$:MeOH (1:1); B: Water; C: 100 mM Ammonium acetate pH 7; gradient: 2 min in 10:85:5, from 10:85:5 to 95:0:5 in 2 min, 5 min in 95:0:5.

B: Column Acquity UPLC BEH C18 2.1×50 mm, 1.7 μm; flow rate 0.61 mL/min; temperature: 35° C., A: $NH_4HCO_3$ 10 mM; B: ACN; gradient: 0.3 min in 98% A, 98% A to 5% A in 2.52 min, 1.02 min in 5% A, 5% A to 98% A in 0.34 min, 0.57 min in 98% A.

Intermediate 1. Methyl 1-(2-phenylethyl)piperidine-4-carboxylate

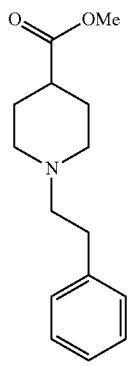

$K_2CO_3$ (5.94 g, 42.95 mmol) and KI (1.19 g, 7.16 mmol) were added to a solution of methyl piperidine-4-carboxylate (4.10 g, 28.63 mmol) and 2-bromoethylbenzene (4.65 mL, 34.36 mmol) in ACN (80 mL). The reaction mixture was refluxed for 3.5 h, allowed to reach r.t. and solvent was concentrated off. The residue was diluted with $H_2O$ (50 mL) and extracted with DCM (2×40 mL). The combined organic layers were dried over anh. $Na_2SO_4$, filtered and concentrated. The crude residue was flash chromatographed on $SiO_2$ (DCM and 1→10% MeOH/DCM), to give an oil that was purified again by flash chromatography on $SiO_2$ (1→8% MeOH/DCM), to afford the title compound as a yellow solid (4.13 g, yield 58%).

$^1$H-NMR (CDCl$_3$, 250 MHz, δ): 7.46-7.11 (m, 5H, ArH); 3.68 (s, 3H, CH$_3$); 3.06-2.90 (m, 2H, CH$_2$); 2.88-2.75 (m, 2H, CH$_2$); 2.67-2.52 (m, 2H, CH$_2$); 2.33 (m, 1H, CH); 2.19-1.71 (m, 6H, CH$_2$).

Intermediate 2A. Methyl 4-benzyl-1-(2-phenylethyl)piperidine-4-carboxylate

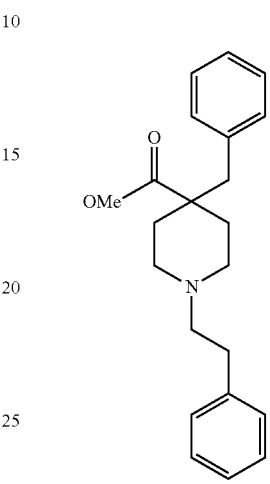

Methyl 1-(2-phenylethyl)piperidine-4-carboxylate (intermediate 1, 2.0 g, 8.09 mmol) in THF (25 mL) was added to a freshly prepared −5° C. cooled solution of LDA (0.36 M, 27 mL, 9.65 mmol). The resulting mixture was stirred at −5° C. for 30 min, and a solution of bromomethylbenzene (0.97 mL, 8.09 mmol) in THF (20 mL) was added. The mixture was allowed to reach r.t., and stirred at this temperature for 2.5 h. The reaction mixture was poured into $H_2O$ (40 mL) and solvent was concentrated off. The aqueous residue was extracted with DCM, the combined organic layers were dried over anh. $Na_2SO_4$, filtered and concentrated. The crude was flash chromatographed on $SiO_2$ (DCM and 1→5% MeOH/DCM), to give the title compound as a yellow solid (2.49 g, yield 91%).

$^1$H-NMR (CDCl$_3$, 250 MHz, δ): 7.32-7.13 (m, 8H, ArH); 7.08-6.99 (m, 2H, ArH); 3.63 (s, 3H, CH$_3$); 2.96-2.73 (m, 6H, CH$_2$); 2.61-2.50 (m, 2H, CH$_2$); 2.23-1.98 (m, 4H, CH$_2$); 1.73-1.57 (m, 2H, CH$_2$).

This method was used for the preparation of intermediate 2B using methyl 1-benzylpiperidine-4-carboxylate instead of methyl 1-(2-phenylethyl)piperidine-4-carboxylate.

| INT | Structure | Chemical name | Method | Ret (min) | MS (M + H) |
|---|---|---|---|---|---|
| 2B | 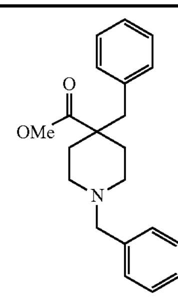 | methyl 1,4-dibenzyl-piperidine-4-carboxylate | B | 2.39 | 324.2 |

Intermediate 3A.
4-Benzyl-1-(2-phenylethyl)piperidine-4-carboxylic Acid Hydrochloride

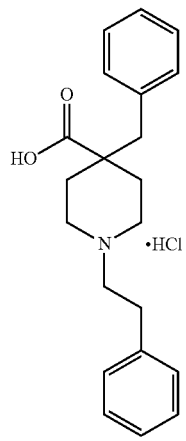 [SMILES: O=C(O)C1(Cc2ccccc2)CCN(CCc2ccccc2)CC1 ; Cl]

A suspension of methyl 4-benzyl-1-(2-phenylethyl)piperidine-4-carboxylate (intermediate 2A, 2.49 g, 7.38 mmol) in HCl (37% aqueous solution, 50 mL) was refluxed for 22 h. The suspension was allowed to reach r.t., and solvent was concentrated off. The crude residue was slurred with EtOH (20 mL) and the solvent was eliminated again, to give the title compound as a brown solid (2.5 g, yield 94%).

$^1$H-NMR (DMSO-$d_6$, 250 MHz, δ): 12.94 (bs, 1H); 10.96 (bs, 0.3H); 10.71 (bs, 0.7H); 7.51-7.00 (m, 10H, ArH); 3.62-2.94 (m, 7H); 2.93-2.66 (m, 3H); 2.20-2.00 (m, 2H, CH$_2$); 1.99-1.74 (m, 2H, CH$_2$).

This method was used for the preparation of intermediate 3B using intermediate 2B as a starting material:

| INT | Structure | Chemical name | Method | Ret (min) | MS (M + H) |
|---|---|---|---|---|---|
| 3B | 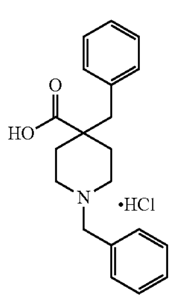 [SMILES: O=C(O)C1(Cc2ccccc2)CCN(Cc2ccccc2)CC1 ; Cl] | 1,4-dibenzyl-piperidine-4-carboxylic acid hydrochloride | B | 1.11 | 310.2 |

Intermediate 4A. 1'-(2-Phenylethyl)spiro[indene-2,4'-piperidin]-1(3H)-one

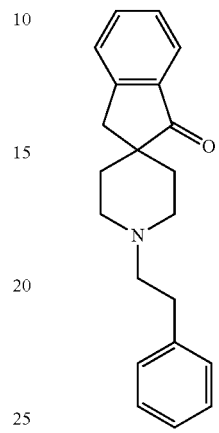

A mixture of 4-benzyl-1-(2-phenylethyl)-piperidine-4-carboxylic acid hydrochloride (intermediate 3A, 1.0 g, 2.78 mmol) and PPA (19.06 g) was warmed up to 130° C. and stirred at this temperature for 2 h. The reaction mixture was allowed to reach 50° C., poured into ice, taken up to pH=8-9 with NaOH (6.0 M aqueous solution) and extracted with Et$_2$O and DCM. The combined organic layers were dried over anh. Na$_2$SO$_4$, filtered and concentrated. The resulting solid was slurred with hexanes, to give the title compound as a brown solid (0.81 g, yield 95%).

$^1$H-NMR (CDCl$_3$, 250 MHz, δ): 7.77 (d, J=7.6 Hz, 1H, ArH); 7.60 (m, 1H, ArH); 7.50-7.17 (m, 7H, ArH); 3.12-2.99 (m, 4H, CH$_2$); 2.91-2.79 (m, 2H, CH$_2$); 2.70-2.60 (m, 2H, CH$_2$); 2.30-2.16 (m, 2H, CH$_2$); 2.16-2.01 (m, 2H, CH$_2$); 1.50-1.36 (m, 2H, CH$_2$).

This method was used for the preparation of intermediate 4B using intermediate 3B as a starting material:

| INT | Structure | Chemical name | Method | Ret (min) | MS (M + H) |
|---|---|---|---|---|---|
| 4B | 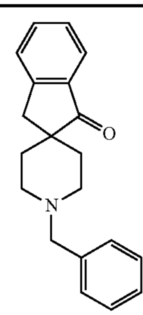 | 1'-benzylspiro[indene-2,4'-piperidin]-1(3H)-one | B | 2.11 | 292.2 |

Intermediate 5A. 1'-(2-Phenylethyl)spiro[indene-2,4'-piperidin]-1(3H)-one oxime

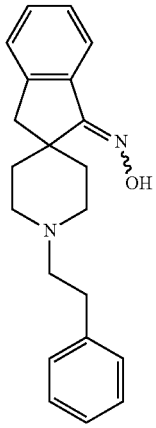 [SMILES: ON=C1c2ccccc2CC12CCN(CCc1ccccc1)CC2]

Pyridine (1 mL, 12.77 mmol) was added to a suspension of 1'-(2-phenylethyl)spiro[indene-2,4'-piperidin]-1(3H)-one (intermediate 4A, 800 mg, 2.62 mmol) and $NH_2OH \cdot HCl$ (364 mg, 5.24 mmol) in EtOH (10 mL) and the mixture was stirred at reflux temperature overnight. The resulting solution was allowed to reach r.t. and NaOH (10% aqueous solution, 2 mL) was added. The suspension was filtered, the solid was rinsed with $H_2O$ and dried under reduced pressure, to give the title compound as a white solid (798 mg, yield 95%).

1H-NMR (DMSO-d6, 250 MHz, δ): 11.11 (bs, 1H, OH); 8.30 (d, J=7.6 Hz, 1H, ArH); 7.45-7.10 (m, 8H, ArH); 3.01-2.82 (m, 4H, CH2); 2.81-2.69 (m, 2H, CH2); 2.59-2.45 (m, 2H, CH2); 2.25-2.04 (m, 2H, CH2); 1.97-1.74 (m, 2H, CH2); 1.57-1.40 (m, 2H, CH2).

HPLC-MS (Method A): Ret, 6.786 min; $ESI^+$-MS m/z: 321.0 (M+1).

This method was used for the preparation of intermediate 5B using intermediate 4B as a starting material:

| INT | Structure | Chemical name | Method | Ret (min) | MS (M + H) |
|---|---|---|---|---|---|
| 5B | 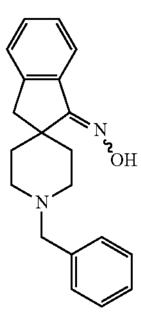 [SMILES: ON=C1c2ccccc2CC12CCN(Cc1ccccc1)CC2] | 1'-benzylspiro[indene-2,4'-piperidin]-1(3H)-one oxime | B | 2.02 | 307.2 |

Example 1. 1'-(2-Phenylethyl)-2,4-dihydro-1H-spiro[isoquinoline-3,4'-piperidin]-1-one

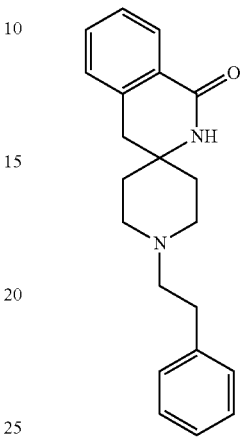

1'-(2-Phenylethyl)spiro[indene-2,4'-piperidin]-1(3H)-one oxime (intermediate 5A, 750 mg, 2.34 mmol) was added to a 130° C. heated solution of PPA (19.07 g), and the resulting suspension was stirred at 130° C. until a homogeneous mixture was obtained (4 h). The reaction mixture was allowed to reach 55° C., poured into ice, taken up to pH=8-9 with NaOH (9.0 M aqueous solution, 30 mL) and extracted with DCM. The combined organic layers were dried over anh. $Na_2SO_4$, filtered and concentrated, to give a brown coloured solid. This solid was slurred with hexanes, to give the title compound as a brown solid (381 mg, yield 56%).

HPLC-MS (Method A): Ret, 8.753 min; $ESI^+$-MS m/z: 321.0 (M+1).

This method was used for the preparation of example 2 using intermediate 5B as a starting material:

| INT | Structure | Chemical name | Method | Ret (min) | MS (M + H) |
|---|---|---|---|---|---|
| 2 | 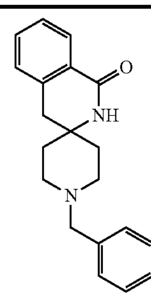 | 1'-benzyl-2,4-dihydro-1H-spiro[isoquinoline-3,4'-piperidin]-1-one | B | 1.74 | 307.1 |

Example 3. 1'-(2-Phenylethyl)-2,4-dihydro-1H-spiro[isoquinoline-3,4'-piperidine]

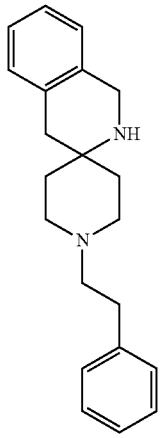

BH$_3$.SMe$_2$ (0.20 mL, 2.07 mmol) was added to a suspension of 1'-(2-phenylethyl)-2H-spiro[isoquinoline-3,4'-piperidin]-1(4H)-one (example 1, 265 mg, 0.83 mmol) in toluene (10 mL) and the mixture was stirred at reflux temperature overnight. The reaction mixture was allowed to reach r.t., HCl (15% aqueous solution, 0.50 mL) was added and it was stirred for 20 min at r.t. MeOH (8 mL) was added, the mixture was refluxed for 30 min, allowed to reach r.t., and the solvent was concentrated off. The residue was suspended in H$_2$O (10 mL), basified with NaOH (10% aqueous solution, 5 mL) and extracted with DCM. The combined organic layers were dried over anh. Na$_2$SO$_4$, filtered and concentrated. The crude residue was flash chromatographed on SiO$_2$ (5→10% MeOH/AcOEt and 90:10:1 AcOEt/MeOH/NH$_4$OH), to give a colourless oil, which was slurred with cold hexanes (−10° C.) and cold Et$_2$O (−10° C.), to give the title compound as a white solid (103 mg, yield 41%).

HPLC-MS (Method A): Ret, 8.716 min; ESI$^+$-MS m/z: 306.6 (M+1).

This method was used for the preparation of example 4 using example 2 as a starting material:

| INT | Structure | Chemical name | Method | Ret (min) | MS (M + H) |
|---|---|---|---|---|---|
| 4 | 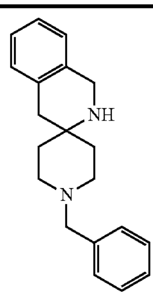 | 1'-benzyl-2,4-dihydro-1H-spiro[isoquinoline-3,4'-piperidine] | B | 1.76 | 293.2 |

Example 5. 1-[1'-(2-Phenylethyl)-1H-spiro[isoquinoline-3,4'-piperidine]-2(4H)-yl]ethanone

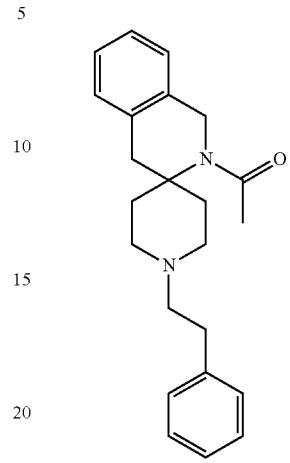

Acetic anhydride (0.22 mL, 2.28 mmol) was added to a solution of 1'-(2-phenylethyl)-1,4-dihydro-2H-spiro[isoquinoline-3,4'-piperidine] (example 3, 140 mg, 0.46 mmol) and pyridine (0.18 mL, 2.28 mmol) in DCM (10 mL) and the mixture was stirred at reflux temperature overnight. The mixture was allowed to reach r.t., poured into H$_2$O (20 mL), basified with NaOH (10% aqueous solution, 3 mL) and extracted with DCM (2×20 mL). The combined organic layers were washed with NaOH (10% aqueous solution, 1×20 mL), dried over Na$_2$SO$_4$ (anhydrous), filtered and concentrated. The crude residue was flash chromatographed on SiO$_2$ (1→5% MeOH/DCM), to give a colourless oil, which was slurred with cold hexanes (−10° C.) and with cold Et$_2$O (−10° C.), to give the title compound as a white solid (111 mg, yield 69%).

HPLC-MS (Method A): Ret, 15.446 min; ESI$^+$-MS m/z: 348.9 (M+1).

Example 6. 1'-Benzyl-2-methyl-2,4-dihydro-1H-spiro[isoquinoline-3,4'-piperidine]

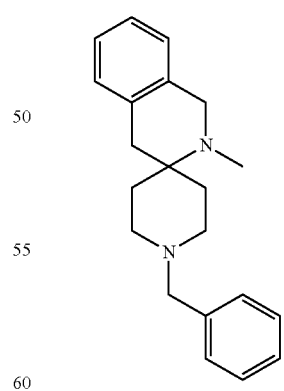

1'-Benzyl-2,4-dihydro-1H-spiro[isoquinoline-3,4'-piperidine] (example 4, 392 mg, 1.3 mmol) was dissolved in MeOH (20 mL), formaldehyde (37% aqueous solution, 4.83 mL, 64 mmol) was added and the solution was stirred at r.t. overnight. Then, sodium triacetoxyborohydride (767 mg, 3.63 mmol) was added and the mixture was stirred at r.t.

overnight. The solvent was concentrated, diluted with NaOH 10% and extracted with ethyl acetate. The combined organic layers were washed with water, dried with anh. $Na_2SO_4$, filtered and concentrated to afford the title compound as a colourless oil (321 mg, yield 72%).

HPLC-MS (Method B): Ret, 2.01 min; ESI$^+$-MS m/z: 307.2 (M+1).

Example 7. 4-(2-(2-Methyl-2,4-dihydro-1H-spiro[isoquinoline-3,4'-piperidine]-1'-yl)ethyl)morpholine

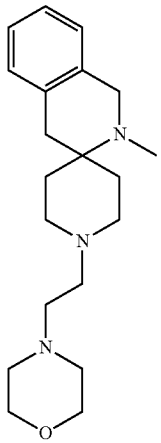 [SMILES: CN1Cc2ccccc2CC12CCN(CCN1CCOCC1)CC2]

a) 2-Methyl-2,4-dihydro-1H-spiro[isoquinoline-3,4'-piperidine]

A mixture of 1'-benzyl-2-methyl-2,4-dihydro-1H-spiro[isoquinoline-3,4'-piperidine] (example 6, 214 mg, 0.7 mmol), AcOH (4 µL) and Pd(OH)$_2$ (140 mg, 20% wt on charcoal) in MeOH (6 mL) was stirred under H$_2$ atmosphere overnight. The solids were filtered off and the solvent was evaporated to dryness to give the title compound as a crude product (163 mg, yield 89%) that was used in the following step without further purification.

HPLC-MS (Method B): Ret, 1.08 min; ESI$^+$-MS m/z: 217.1 (M+1).

b) Title Compound 4-(2-Chloroethyl)morpholine hydrochloride (31 mg, 0.09 mmol) was added to a suspension of 2-methyl-2,4-dihydro-1H-spiro[isoquinoline-3,4'-piperidine] (obtained in step a, 80 mg, 0.37 mmol), $K_2CO_3$ (153 mg, 1.1 mmol) and NaI (28 mg, 0.18 mmol) in ACN (10 mL). The reaction mixture was stirred at 100° C. overnight and it was cooled down to room temperature. Then, the solvent was concentrated, diluted with water and extracted with ethyl acetate. The combined organic layers were washed with water, dried with anh. $Na_2SO_4$, filtered and concentrated. The crude residue was purified by flash chromatography on SiO$_2$ (DCM and 1→50% MeOH/DCM) to afford the title compound as a yellow oil (31 mg, yield 25%).

HPLC-MS (Method B): Ret, 1.34 min; ESI$^+$-MS m/z, 330.2 (M+1).

Table of Examples with Binding to the σ$_1$-Receptor:
Biological Activity
Pharmacological Study
Human σ$_1$ Receptor Radioligand Assay To investigate binding properties of test compounds to human σ$_1$ receptor, transfected HEK-293 membranes and [$^3$H](+)-pentazocine (Perkin Elmer, NET-1056), as the radioligand, were used. The assay was carried out with 7 µg of membrane suspension, 5 nM of [$^3$H](+)-pentazocine in either absence or presence of either buffer or 10 µM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail Results:

As this invention is aimed at providing a compound or a chemically related series of compounds which act as ligands of the σ$_1$ receptor it is a very preferred embodiment in which the compounds are selected which act as ligands of the σ$_1$ receptor and especially compounds which have a binding expressed as $K_i$ which is preferably <1000 nM, more preferably <500 nM, even more preferably <100 nM.

The following scale as been adopted for representing the binding to the σ$_1$ receptor expressed as $K_i$:
+$K_i$-σ$_1$>=500 nM
++$K_i$-σ$_1$<500 nM
+++$K_i$-σ$_1$<100 nM All compounds prepared in the present application exhibit binding to the σ$_1$ receptor, in particular the following binding results are shown:

| EX | $K_i$-σ$_1$ |
|---|---|
| 1 | +++ |
| 2 | +++ |
| 3 | +++ |
| 4 | +++ |
| 5 | ++ |
| 6 | +++ |
| 7 | ++ |

The invention claimed is:
1. A compound of formula (I):

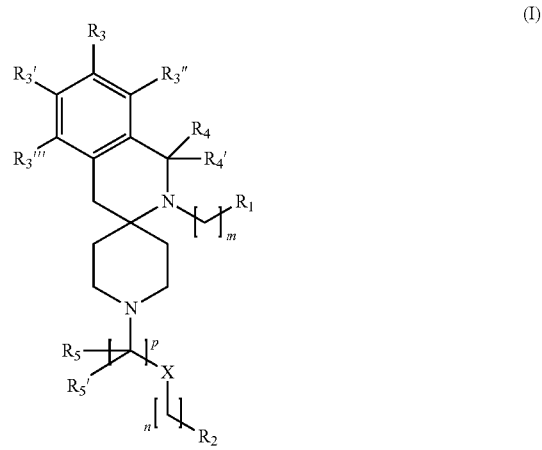

wherein
m is 0, 1, 2, 3, 4, 5 or 6;
n is 0, 1, 2, 3 or 4;

p is 1, 2, 3 or 4;

$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted heterocyclyl, —C(O)$R_6$, —C(O)O$R_6$, —C(O)N$R_6R_{6'}$ and —S(O)$_2R_6$;

wherein $R_6$ and $R_{6'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl or substituted or unsubstituted alkylaryl, substituted or unsubstituted cycloalkyl or substituted or unsubstituted alkylcycloalkyl, and substituted or unsubstituted heterocyclyl or substituted or unsubstituted alkyheterocylcyl;

$R_2$ is selected from substituted or unsubstituted cycloalkyl, substituted or unsubstituted aryl and substituted or unsubstituted heterocyclyl;

wherein said cycloalkyl, aryl or heterocyclyl in $R_2$, if substituted, is substituted with one or more substituent/s selected from halogen, —$R_{12}$, —O$R_{12}$, —NO$_2$, —N$R_{12}R_{12'''}$, N$R_{12}$C(O)$R_{12'}$, —S(O)$_2$N$R_{12}R_{12'}$, —N$R_{12}$C(O)N$R_{12'}R_{12''}$, —S$R_{12}$, —S(O)$R_{12}$, S(O)$_2R_{12}$, —CN, haloalkyl, haloalkoxy, —C(O)O$R_{12}$, —C(O)N$R_{12}R_{12'}$, and —N$R_{12}$S(O)$_2$N$R_{12'}R_{12''}$;

wherein, said cycloalkyl or non-aromatic heterocyclyl in $R_2$, if substituted, may also be substituted with

or =O;

wherein $R_{12}$, $R_{12'}$ and $R_{12''}$ are independently selected from hydrogen, unsubstituted $C_{1-6}$ alkyl, and unsubstituted $C_{2-6}$ alkenyl, unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

X is selected from a bond, —C($R_xR_{x'}$)— and —C($R_x$)(O$R_7$)—;

$R_x$ is selected from hydrogen, substituted or unsubstituted $C_{1-6}$ alkyl, substituted or unsubstituted $C_{2-6}$ alkenyl, substituted or unsubstituted $C_{2-6}$ alkynyl, —C(O)O$R_7$, —C(O)N$R_7R_{7'}$, —N$R_7$C(O)$R_7$, and —N$R_7R_{7'''}$;

$R_{x'}$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_7$ and $R_{7'}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{7'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ is selected from hydrogen, halogen, —$R_9$, —O$R_9$, —NO$_2$, —N$R_9R_{9'''}$, —N$R_9$C(O)$R_{9'}$, —NC(O)O$R_9$, —N$R_9$S(O)$_2R_{9'}$, —S(O)$_2$N$R_9R_{9'}$, —N$R_9$C(O)N$R_9R_{9''}$, —S$R_9$, —S(O)$R_9$, —S(O)$_2R_9$, —CN, haloalkyl, haloalkoxy, —C(O)O$R_9$, —C(O)N$R_9R_{9'}$, —N$R_9$S(O)$_2$N$R_{9'}R_{9''}$ and —OC(O)$R_9$;

$R_{3'}$, $R_{3''}$ and $R_{3'''}$ are independently selected from hydrogen, halogen, —$R_9$, —NO$_2$, —N$R_9R_{9'''}$, —N$R_9$C(O)$R_{9'}$, —NC(O)O$R_9$, —N$R_9$S(O)$_2R_{9'}$, —S(O)$_2$N$R_9R_{9'}$, —N$R_9$C(O)N$R_9R_{9''}$, —S$R_9$, —S(O)$R_9$, —S(O)$_2R_9$, —CN, haloalkyl, haloalkoxy, —C(O)O$R_9$, —C(O)N$R_9R_{9'}$, —N$R_9$S(O)$_2$N$R_{9'}R_{9''}$ and —OC(O)$R_9$;

wherein $R_9$, $R_{9'}$ and $R_{9''}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{9'''}$ is selected from hydrogen, unsubstituted $C_{1-6}$ alkyl, unsubstituted $C_{2-6}$ alkenyl, unsubstituted $C_{2-6}$ alkynyl and -Boc;

$R_4$ is selected from hydrogen, —O$R_8$, substituted or unsubstituted $C_{1-6}$ alkyl, substituted or unsubstituted $C_{2-6}$ alkenyl, substituted or unsubstituted $C_{2-6}$ alkynyl, —C(O)O$R_8$, —C(O)N$R_8R_{8'}$, —N$R_8$C(O)$R_{8'}$, —N$R_8R_{8'''}$ and —NC(O)O$R_8$;

$R_{4'}$ is selected from hydrogen, or substituted or unsubstituted $C_{1-6}$ alkyl, substituted or unsubstituted $C_{2-6}$ alkenyl, and substituted or unsubstituted $C_{2-6}$ alkynyl;

wherein $R_8$ and $R_{8'}$ are independently selected from hydrogen, unsubstituted $C_{1-6}$ alkyl, unsubstituted $C_{2-6}$ alkenyl, and unsubstituted $C_{2-6}$ alkynyl;

and wherein $R_{8'''}$ is selected from hydrogen, unsubstituted $C_{1-6}$ alkyl, unsubstituted $C_{2-6}$ alkenyl, unsubstituted $C_{2-6}$ alkynyl and -Boc;

alternatively, $R_4$ and $R_{4'}$ may form together with the carbon to which they are attached, a C=O group;

$R_5$ and $R_{5'}$ are independently selected from hydrogen, or substituted or unsubstituted $C_{1-6}$ alkyl, substituted or unsubstituted $C_{2-6}$ alkenyl, and substituted or unsubstituted $C_{2-6}$ alkynyl;

or a stereoisomer, an enantiomer or a diastereomer thereof, or a racemate thereof, or a mixture in any mixing ratio of two stereoisomers, enantiomers and/or diastereomers thereof, or a salt or a solvate thereof;

wherein the following compound is excluded:

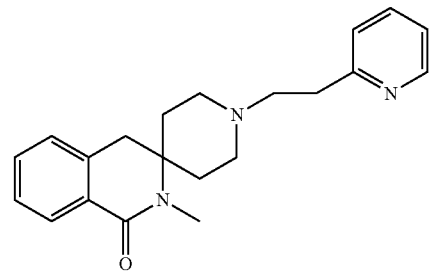 [SMILES: CN1C(=O)c2ccccc2CC12CCN(CCc1ccccn1)CC2]

or a salt thereof.

2. The compound according to claim 1, wherein
m is 0 or 1, n is 0 or 1 and p is 1.

3. The compound according to claim 1, wherein
$R_1$ is selected from hydrogen, substituted or unsubstituted $C_{1-6}$ alkyl, substituted or unsubstituted $C_{2-6}$ alkenyl, substituted or unsubstituted $C_{2-6}$ alkynyl, and —C(O)$R_6$;

and wherein $R_6$ is selected from hydrogen, substituted or unsubstituted $C_{1-6}$ alkyl, substituted or unsubstituted $C_{2-6}$ alkenyl, and substituted or unsubstituted $C_{2-6}$ alkynyl.

4. The compound according to claim 1, wherein
$R_2$ is selected from substituted or unsubstituted aryl and substituted or unsubstituted heterocyclyl.

5. The compound according to claim 1, wherein
X is selected from a bond and —(CR$_x$R$_{x'}$)—; and wherein
R$_x$ is selected from hydrogen, substituted or unsubstituted C$_{1-6}$ alkyl, substituted or unsubstituted C$_{2-6}$ alkenyl, and substituted or unsubstituted C$_{2-6}$ alkynyl;
R$_{x'}$ is selected from hydrogen, substituted or unsubstituted C$_{1-6}$ alkyl, substituted or unsubstituted C$_{2-6}$ alkenyl and substituted or unsubstituted C$_{2-6}$ alkynyl.
6. The compound according to claim 1, wherein
R$_3$ is selected from hydrogen, halogen, —R$_9$, —OR$_9$, and —NR$_9$R$_{9'''}$; and
R$_{3'}$, R$_{3''}$ and R$_{3'''}$ are independently selected from hydrogen, halogen, —R$_9$, and —NR$_9$R$_{9'''}$;
wherein R$_9$, R$_{9'}$ and R$_{9''}$ are independently selected from hydrogen, unsubstituted C$_{1-6}$ alkyl, unsubstituted C$_{2-6}$ alkenyl, and unsubstituted C$_{2-6}$ alkynyl; and
R$_{9'''}$ is selected from hydrogen, unsubstituted C$_{1-6}$ alkyl, unsubstituted C$_{2-6}$ alkenyl, unsubstituted C$_{2-6}$ alkynyl and -Boc.
7. The compound according to claim 1, wherein
R$_4$ is selected from hydrogen, —OR$_8$, substituted or unsubstituted C$_{1-6}$ alkyl;
R$_{4'}$ is selected from hydrogen, or substituted or unsubstituted C$_{1-6}$ alkyl;
and wherein R$_8$ is selected from hydrogen, unsubstituted C$_{1-6}$ alkyl, unsubstituted C$_{2-6}$ alkenyl, and unsubstituted C$_{2-6}$ alkynyl;
or
R$_4$ and R$_{4'}$ form together with the carbon to which they are attached, a C=O group.
8. The compound according to claim 1, wherein X is a bond.
9. The compound according to claim 1, wherein
m is 0 or 1;
n is 0 or 1;
p is 1;
R$_1$ is selected from hydrogen, substituted or unsubstituted C$_{1-6}$ alkyl, and —C(O)R$_6$;
R$_2$ is selected from substituted or unsubstituted aryl and substituted or unsubstituted heterocyclyl;
X is a bond;
R$_3$, R$_{3'}$, R$_{3''}$ and R$_{3'''}$ are all hydrogen;
R$_4$ and R$_{4'}$ are both hydrogen, or may form together with the carbon to which they are attached, a C=O group;
R$_5$ and R$_{5'}$ are both hydrogen;
and
R$_6$ is substituted or unsubstituted C$_{1-6}$ alkyl.
10. The compound according to claim 9, wherein R$_1$ is substituted or unsubstituted methyl.
11. The compound according to claim 9, wherein R$_2$ is substituted or unsubstituted phenyl or substituted or unsubstituted morpholine.
12. The compound according to claim 9, wherein R$_6$ is substituted or unsubstituted methyl.
13. The compound according to claim 1, wherein the compound is selected from:
1'-phenethyl-2,4-dihydro-1H-spiro[isoquinoline-3,4'-piperidin]-1-one,
1'-benzyl-2,4-dihydro-1H-spiro[isoquinoline-3,4'-piperidin]-1-one,
1'-phenethyl-2,4-dihydro-1H-spiro[isoquinoline-3,4'-piperidine],
1'-benzyl-2,4-dihydro-1H-spiro[isoquinoline-3,4'-piperidine],
1-(1'-phenethyl-1H-spiro[isoquinoline-3,4'-piperidine]-2(4H)-yl)ethanone,
1'-benzyl-2-methyl-2,4-dihydro-1H-spiro[isoquinoline-3,4'-piperidine] and
4-(2-(2-methyl-2,4-dihydro-1H-spiro[isoquinoline-3,4'-piperidine]-1'-yl)ethyl)morpholine.

14. A process for the preparation of the compound of Formula (I) according to claim 1, which comprises reacting a compound of Formula (Ib')

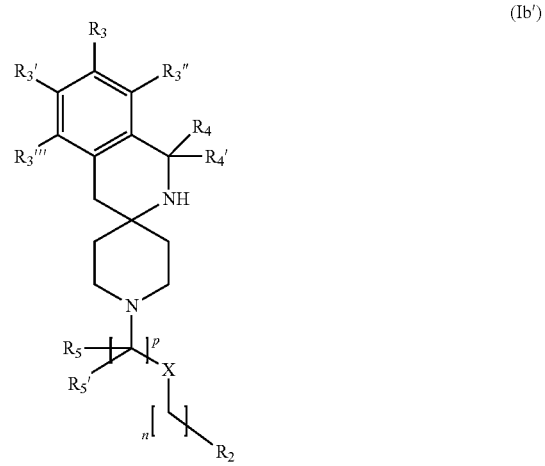

(Ib')

with a compound of Formula (XIa) in an alkylating reaction, (XIb) in a reductive amination reaction, (XIc) in an acylation reaction or (XId) in an acylation reaction

XIa

XIb

XIc

XId wherein m, n, p, R$_1$, R$_2$, R$_3$, R$_{3'}$, R$_{3''}$, R$_{3'''}$, R$_4$, R$_{4'}$, R$_5$, R$_{5'}$, R$_6$ and X have the meaning as defined in claim 1 for the compound of Formula (I), L is a leaving group and W is chloro, bromo, —OH, —O-methyl or —O-ethyl.

15. A process for the preparation of the compound of Formula (I) according to claim 1, employing a compound of Formula IIa, IIb, III, IVa, IVb, Va, Vb, VIa, VIb, VIIa, VIIb, VIII, Ia, IX, Ib, X, Ic, XIa, XIb, XIc, XId, XII, XIIIa, XIIIb, XIV, XV, XVI, XVII, XVII', Ib', X', Ic', IX' or Ib':

-continued

IIa (P = PG)
IIb (P = Y)

III

IVa (P = PG)
IVb (P = Y)

Va (P = PG)
Vb (P = Y)

VIa (P = PG)
VIb (P = Y)

VIIa (P = PG)
VIIb (P = Y)

VIII (P = PG)
Ia (P = Y)

IX (P = PG)
Ib (P = Y)

X (P = PG)
Ic (P = Y)

XIa

XIb

XIc

XId

XII

XIIIa

XIIIb

XIV

-continued
XV
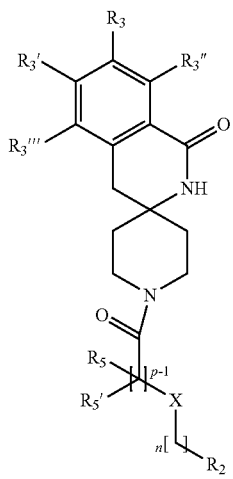
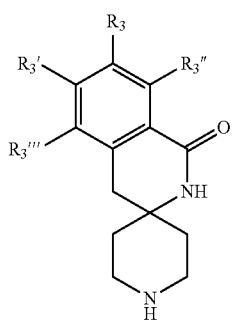
XVII
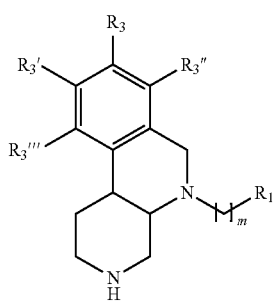
(XVII')
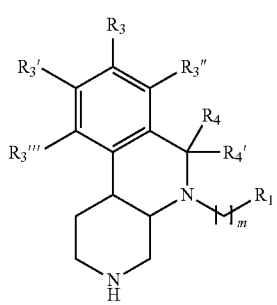
-continued
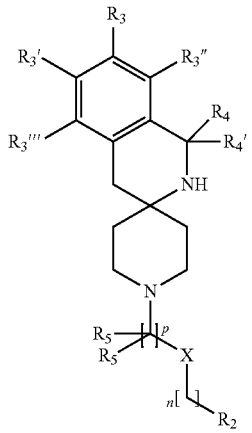
(Ib')
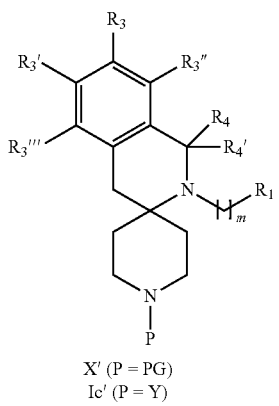
X' (P = PG)
Ic' (P = Y)
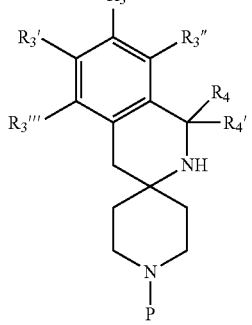
IX' (P = PG)
Ib' (P = Y)
wherein m, n, p, $R_1$, $R_2$, $R_3$, $R_3{'}$, $R_3{''}$, $R_3{'''}$, $R_4$, $R_4{'}$, $R_5$, $R_5{'}$, $R_6$ and X have the meaning as defined in claim 1 for the compound of Formula (I), L is a leaving group, W is chloro, bromo, —OH, —O-methyl or —O-ethyl, PG is a protecting group and Y is
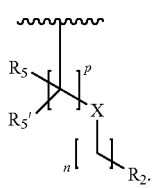

16. A pharmaceutical composition which comprises the compound according to claim 1, or a pharmaceutically acceptable salt thereof, and a pharmaceutically acceptable carrier, adjuvant or vehicle.

17. A method of treating a sigma-1 ($\sigma_1$) receptor related disease in a subject in need thereof, comprising administration of an effective amount of the compound according to claim 1.

18. A method of treating pain in a subject in need thereof, comprising administration of an effective amount of the compound according to claim 1.

19. The method according to claim 18, wherein the pain is medium to severe pain, visceral pain, chronic pain, cancer pain, migraine, inflammatory pain, acute pain or neuropathic pain, allodynia, or hyperalgesia.

* * * * *

UNITED STATES PATENT AND TRADEMARK OFFICE
CERTIFICATE OF CORRECTION

PATENT NO. : 10,072,008 B2
APPLICATION NO. : 15/569939
DATED : September 11, 2018
INVENTOR(S) : Carmen Almansa-Rosales Page 1 of 1

It is certified that error appears in the above-identified patent and that said Letters Patent is hereby corrected as shown below:

On the Title Page

FOREIGN PATENT DOCUMENTS, Line 3: "WO 01/12830 A1" should read -- WO 01/12630 --

Signed and Sealed this
Twenty-third Day of October, 2018

Andrei Iancu
*Director of the United States Patent and Trademark Office*